US007358329B2

(12) United States Patent
Morton et al.

(10) Patent No.: US 7,358,329 B2
(45) Date of Patent: Apr. 15, 2008

(54) ANTAGONISTS TO CHAPERONIN 10

(75) Inventors: Halle Morton, Coorparoo (AU); Alice Christina Cavanagh, Ashgrove (AU)

(73) Assignee: The University of Queensland, Queensland (AU)

( * ) Notice: Subject to any disclaimer, the term of this patent is extended or adjusted under 35 U.S.C. 154(b) by 780 days.

(21) Appl. No.: 10/151,006

(22) Filed: May 21, 2002

(65) Prior Publication Data

US 2003/0175280 A1 Sep. 18, 2003

Related U.S. Application Data

(60) Continuation of application No. 09/255,703, filed on Feb. 23, 1999, now Pat. No. 6,417,334, which is a division of application No. 08/654,618, filed as application No. PCT/AU94/00742 on Nov. 30, 1994, now Pat. No. 6,113,899.

(30) Foreign Application Priority Data

Nov. 30, 1993 (AU) .................... PM2705
Sep. 16, 1994 (AU) .................... PM8234

(51) Int. Cl.
*A61K 38/00* (2006.01)
(52) U.S. Cl. ...................................... 530/300
(58) Field of Classification Search ............... 530/300, 530/350
See application file for complete search history.

(56) References Cited

FOREIGN PATENT DOCUMENTS

| WO | 86/05498 | 9/1986 |
|---|---|---|
| WO | WO86/05498 | 9/1986 |
| WO | 88/04779 | 6/1988 |
| WO | WO88/04779 | 6/1988 |

OTHER PUBLICATIONS

Pilkingston et al (DNA Seq. 1993(3):5):291-295).*
Lazar et al. Molecular and Cellular Biology 8:1247-1252, 1988.*
Bowie et al. Science, 247:1306-1310, 1990.*
Cavanagh et al. "The Purification of Early-Pregnancy Factor to Homogeneity From Human Platelets and Identification as Caperonin 10," *Eur. J. Biochem.* (1994), vol. 222, pp. 551-560.
Quinn et al. "Effect of Monoclonal Antibodies To Early Pregnancy Factor (DPF) On the in vivo Growth of Transplantable Murine Tumours," *Cancer Immunol. Immunother.* (1992), vol. 34, pp. 265-271.
Quinn et al. "Monoclonal Antiboidies to Early Pregnancy Factor Perturb Tumour Cell Growth," *Clin. Exp. Immunol.* (1990), vol. 80, pp. 100-108.
Quinn et al. "Early Pregnancy Factor In Liver Regeneration After Partial Hepatectomy in Rats: Relationship with Chaperonin 10," *Hepatology* (1994), vol. 20, pp. 1294-1302.
Hartmann et al. "Identification Of A Mammalian 10-kDa Heat Shock Protein, A Mitrochrondrial Chaperonin 10 Homologue Essential For Assisted Folding of Trimeric Ornithine Transcarbamoylase in vitro," *Proc. Natl. Acad. Sci. USA* (1992), vol. 89, pp. 3394-3398.
Monzini et al. "Identification And Cloning Of Human Chaperonin 10 Homologue," *Biochimica et Biophysica Acta* (1994), vol. 1218, pp. 478-480.
Morton et al. "Early Pregnancy Factor," *Seminars in Reproductive Endocrinology* (1992), vol. 10, pp. 72-82.
Hartman et al. (1993) Biochimica et Biophysica Acta, vol. 1164, No. 2; 219-222.
Cavanaugh and Morton (1993) J. Leukoc. Biol., Suppl.; 48 (abstract)
Athanasis-Platsis et al. (1991) Journal of Reproduction & Fertility, vol. 92, No. 2, 443-451.
Somodevilla-Torres et al., "Preparation and characterization of polyclonal antibodies against human chaperonin 10," Cell Stress and Chaperonins, 2000, 5 (1), 14-20.
Cavanagh et al. "The Purification of Early-Pregnancy Factor to Homogeneity From Human Platelets and Identification as Caperonin 10," *Eur. J. Biochem.* (1994), vol. 222, pp. 551-560.
Quinn et al. "Effect of Monoclonal Antibodies To Early Pregnancy Factor (DPF) On the in vivo Growth of Transplantable Murine Tumours," *Cancer Immunol. Immunother.* (1992), vol. 34, pp. 265-271.
Quinn et al. "Mononclonal Antobodies to Early Pregnancy Factor Perturb Tumour Cell Growth," *Clin. Exp. Immunol.* (1990), vol. 80, pp. 100-108.
Quinn et al. "Early Pregnancy Factor In Liver Regeneration After Partial Hepatectomy in Rats: Relationship With Chaperonin 10," *Hepatology* (1994), vol. 20, pp. 1294-1302.
Hartman et al. "Identification Of A Mammalian 10-kDa Heat Shock Protein, A Mitrochrondrial Chaperonin 10 Homologue Essential For Assisted Folding of Trimeric Ornithine Transcarbamoylase in vitro," *Proc. Natl. Acad. Sci. USA* (1992), vol. 89, pp. 3394-3398.
Monzini et al. "Identification And Cloning Of Human Chaperonin 10 Homologue," *Biochimica et Biophysica Acta* (1994), vol. 1218, pp. 478-480.
Morton et al. "Early Pregnancy Factor," *Seminars in Reproductive Endocrinology* (1992), vol. 10, pp. 72-82.

* cited by examiner

*Primary Examiner*—Christopher H. Yaen
(74) *Attorney, Agent, or Firm*—Foley & Lardner LLP

(57) ABSTRACT

Antibodies raised against recombinant or synthetic cpn10 are disclosed. The cpn10 has the sequence GSMAGQAFRKFLPLFDRVLVERSAA-ETVTKGGIMLPEKSQGKVLQ ATVEAVGSG-SKGKGGEIQPVSVKEGDKVLLPEYGGT-KVVLDDKDYFLFRDGDIL GKYVD (SEQ ID NO:21). Antibodies are raised against either the entire sequence of cpn 10, or a shorter peptide sequence derived from cpn10, such as Ac-AGQAFRKFLPL (SEQ ID NO:2), ACQAFRK-FLPL (SEQ ID NO 1), or EKSQGKVLQAT (SEQ ID NO:3), in which the peptides may have a single amino acid deletion, addition or substitution. The antibodies can be used to terminate pregnancy, suppress tumor cell growth or enhance the immune system.

6 Claims, 20 Drawing Sheets

FIG. 2c

Figure 1A:
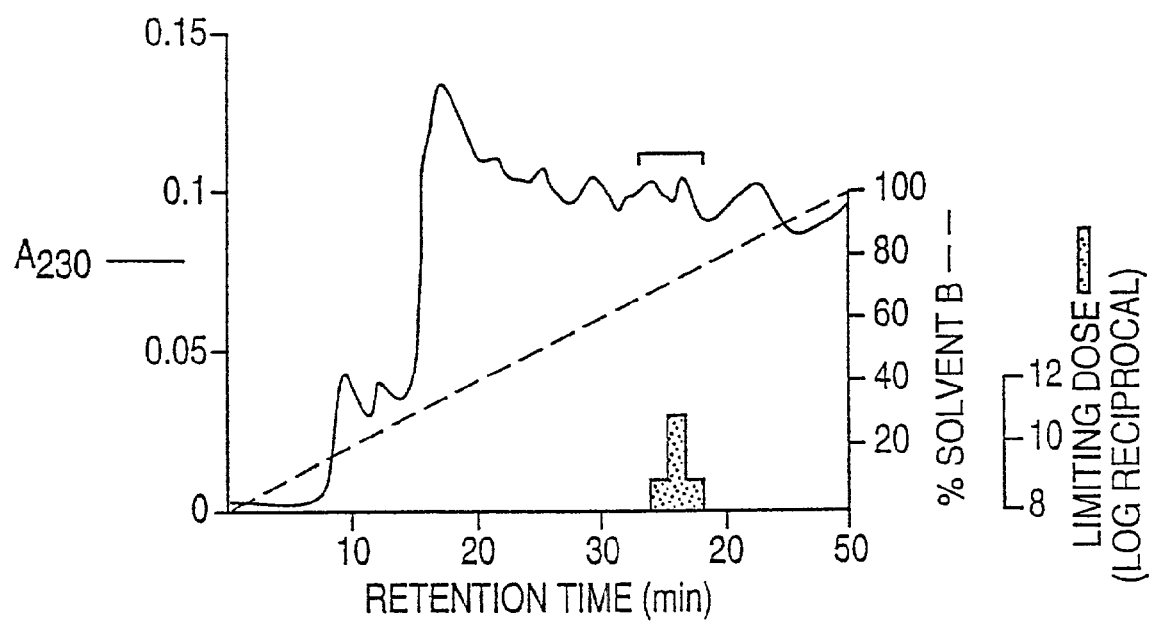

| | | | | | | | | | |
|---|---|---|---|---|---|---|---|---|---|
| Human EPF | | KFLP | LFDRVLVE | | KGGI | MLPEK | KV | LXATVVAVGS | |
| | | | | | AAETVTKGGI | MLPEKSQGKV | KSQGKV | LQATVVAVGX | |
| Rat cpn10 | AC•(AQAGF)RKFLP | LFDRVLVERS | | | | MLPEKSQGKV | | LQATVVAVGS | |
| | 10 | 20 | | 30 | | 40 | | 50 | |

| | | | | | | | | | |
|---|---|---|---|---|---|---|---|---|---|
| Human EPF | GSK | | | EYGGTKV | | VXXXXDXFLF | RDGDILGKYV D | | |
| | GX | | KV | LLPEYGGT | | VLDDKDYFLF | RDGDILGKYV D | | |
| Rat cpn10 | GGKGKGGEIQ | PVXXKXGXXV | | LLPEYGGTKV | | VLDDKDYFLF | RDGDILGKYV D | | |
| | 60 | 70 | | 80 | | 90 | 100 | | |

FIG. 3a
groEL
rhEPF/cpn10
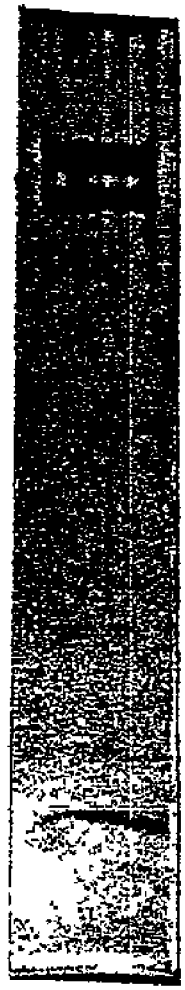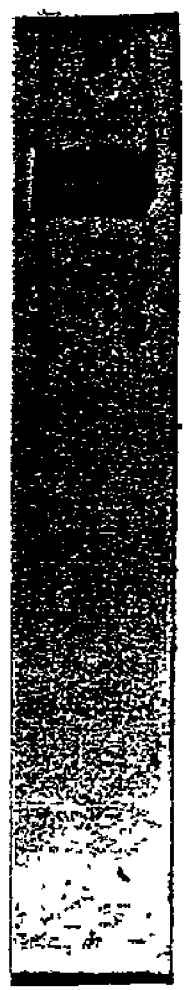
+ATP    -ATP

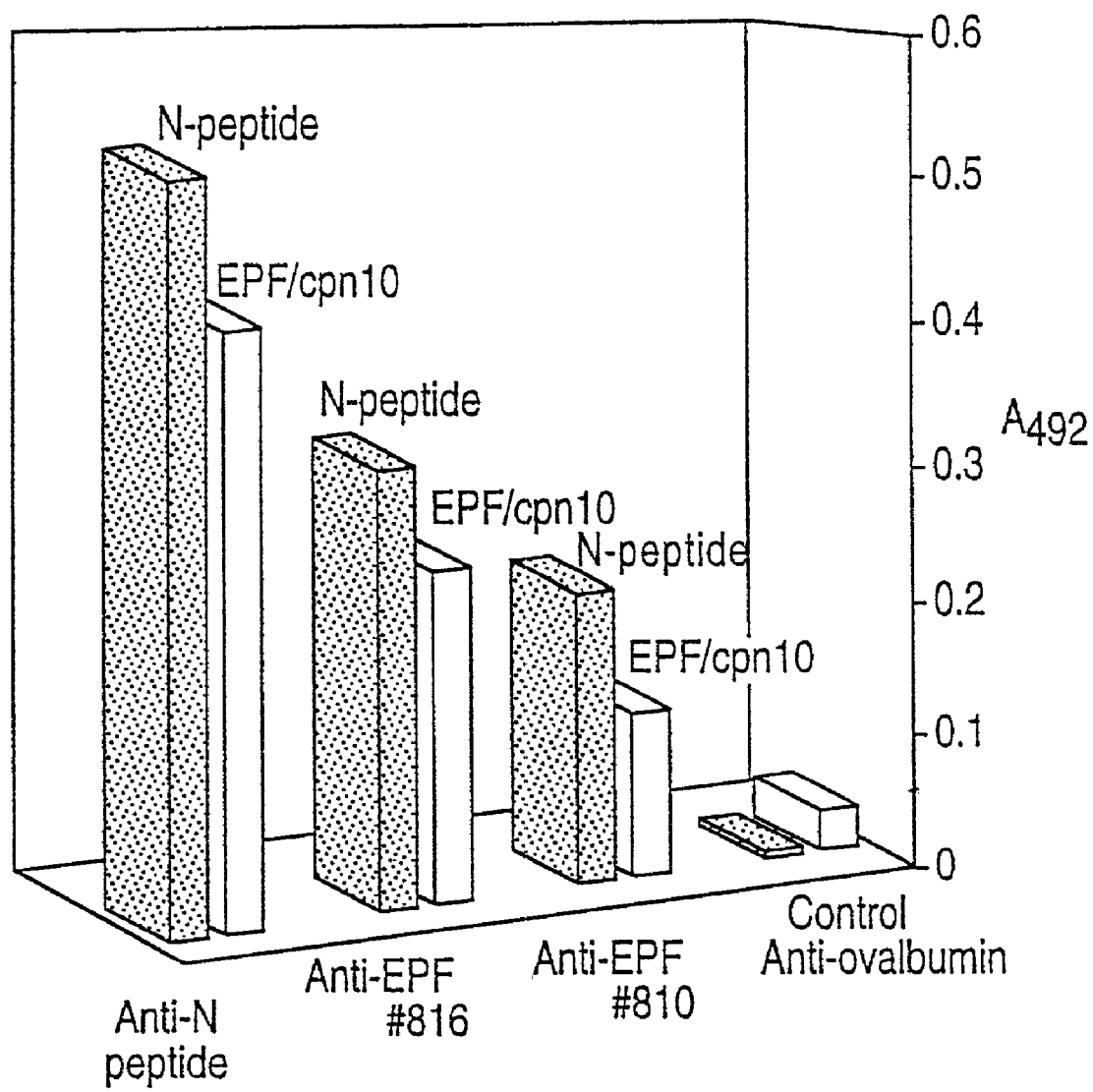

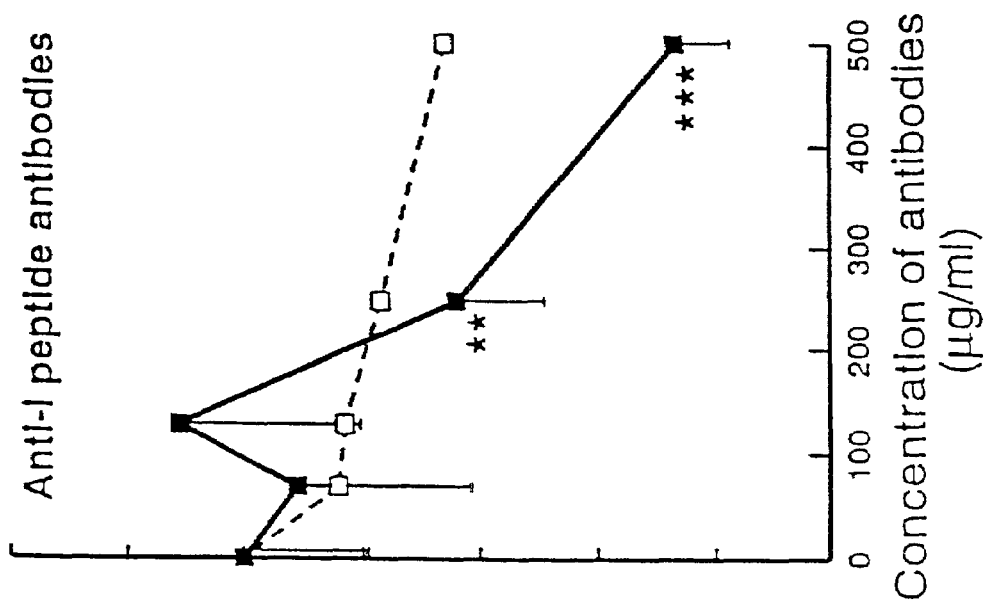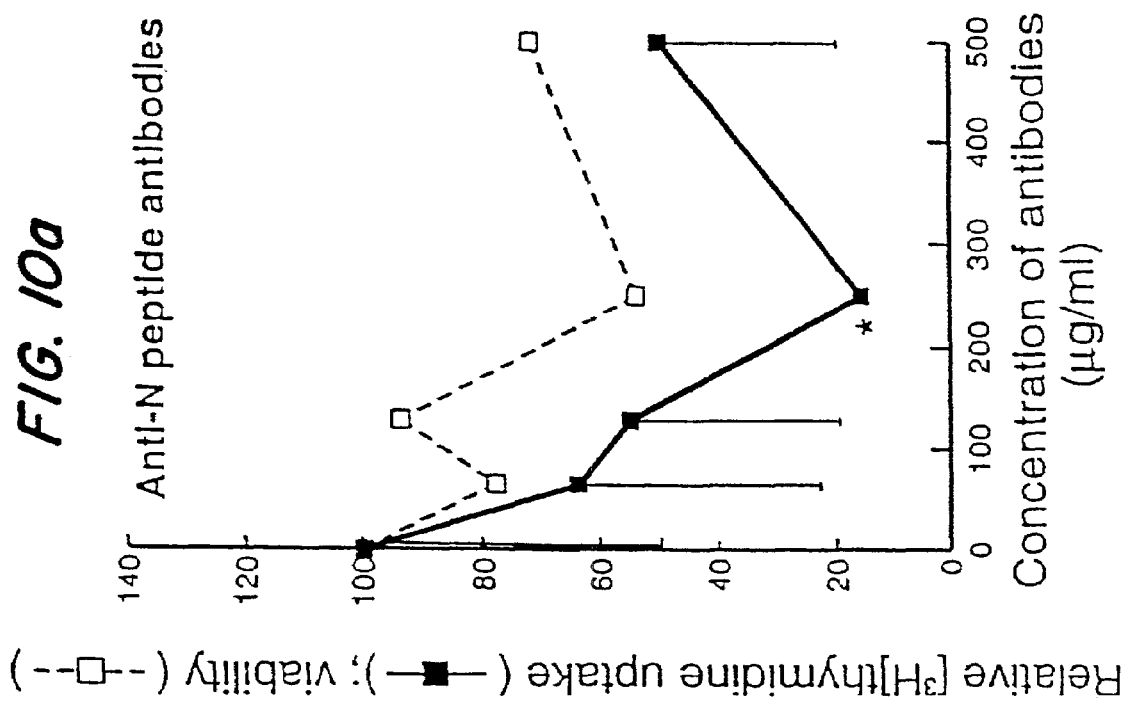

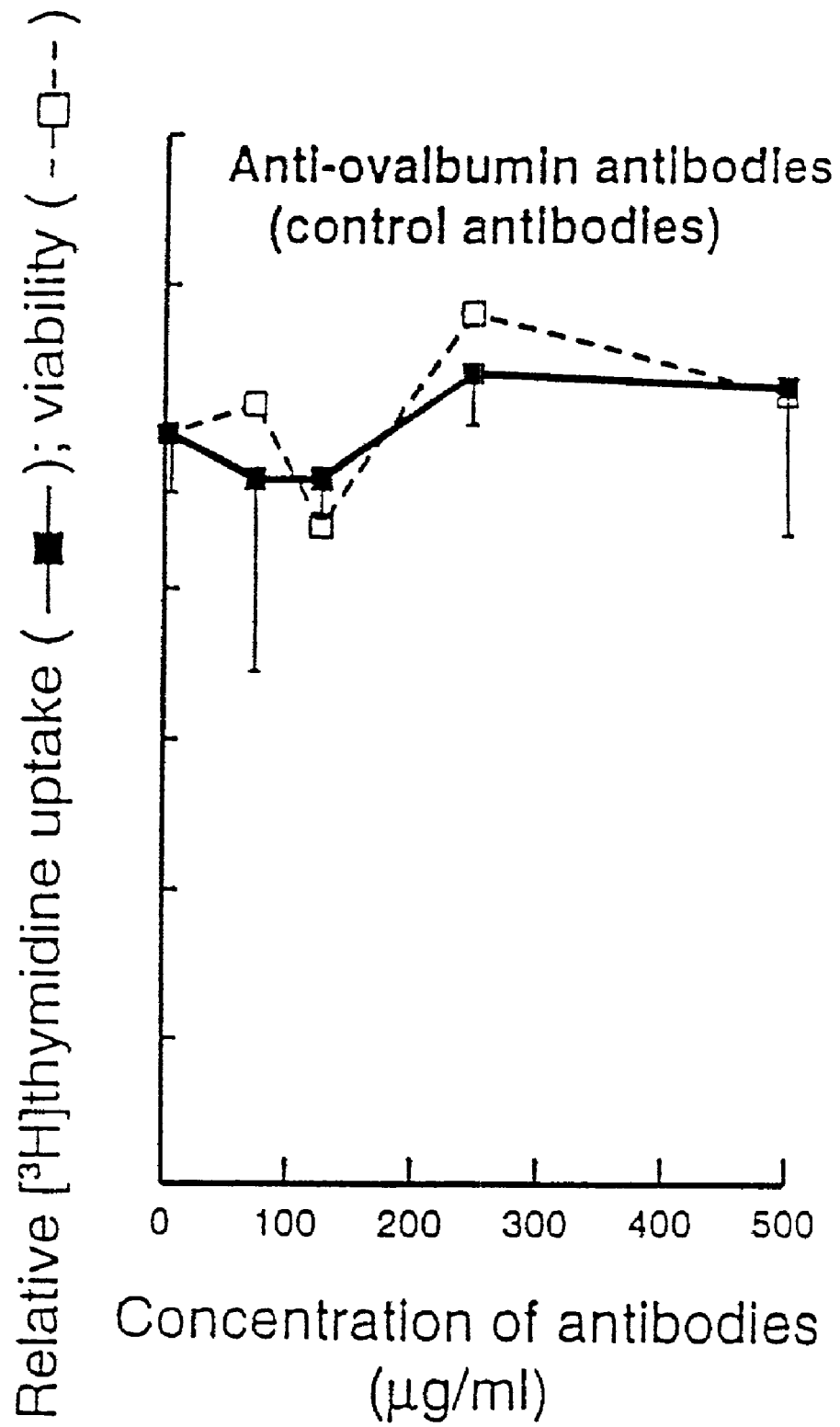

ANTAGONISTS TO CHAPERONIN 10

FIELD OF THE INVENTION

THIS INVENTION relates to antagonists to chaperonin 10 otherwise known as cpn10.

PRIOR ART

Chaperonins belong to a wider class of molecular chaperones, molecules involved in post-translational folding, targeting and assembly of other proteins, but which do not themselves form part of the final assembled structure as discussed by Ellis et al., 1991, Annu. Rev. Biochem. 60 321-347. Most molecular chaperones are "heat shock" or "stress" proteins (hsp); i.e. their production is induced or increased by a variety of cellular insults (such as metabolic disruption, oxygen radicals, inflammation, infection and transformation), heat being only one of the better studies stresses as reviewed by Lindquist et al., 1988, Annu. Rev. Genet. 22 631-677. As well as these quantitative changes in specific protein levels, stress can induce the movement of constitutively produced stress proteins to different cellular compartments as referred to in the Lindquist reference mentioned above. The heat shock response is one of the most highly conserved genetic system known and the various heat shock protein families are among the most evolutionarily stable proteins in existence. As well as enabling cells to cope under adverse conditions, members of these families perform essential functions in normal cells.

There are two types of cpn molecules, cpn60 (monomeric $M_r$ ~60 000) and cpn10 (monomeric $M_r$ ~10 000). Cpn60 has been studied extensively. It has been identified in all bacteria, mitochondria and plastids examined, and a cytoplasmic form, TCP-1, has been identified in eukaryotic cells: its presence on the surface of some cells has been reported, although this has been questioned in the Ellis reference referred to above and also in van Eden, 1991. Immunol. Reviews 121 5-28. Until very recently, cpn10 had been identified only in bacteria but structural and functional equivalents have now been found in chloroplasts (Bertsch et al., 1992, Proceedings of the National Academy of Sciences USA 89 8696-8700) and in rat (Hartman et al., 1992, Proceedings of the National Academy of Sciences USA 89 3394-3398) and bovine liver mitochondria (Lubben et al., 1990, Proceedings of the National Academy of Sciences USA 87 7683-7687).

Cpn60 and cpn10 interact functionally, in the presence of ATP, to mediate protein assembly. Instances of cpn10 acting independently of cpn60 have not yet been reported but cpn60, apparently acting alone, has been implicated in quite disparate events. For example, it is an immuno-dominant target of both antibody and T-cell responses during bacterial infections but, because the protein is so highly conserved, self reactivity is generated. Healthy individuals may use this self-recognition to eliminate transformed and infected autologous cells but defects in control of such recognition may lead to autoimmune disease as discussed by van Eden, 1991, Immunol. Reviews 121 5-28. Not surprisingly, cpn60 has been associated with conditions such as rheumatoid arthritis. There is thus a growing awareness that molecular chaperones, with their capacity to bind to and alter the conformation of a wide variety of polypeptides, may occupy key roles in cellular functions other than protein biogenesis. Reference may also be made to Hartman et al., 1993, Proceedings of the National Academy of Sciences USA 90 2276-2280 which describes the stabilization of protein molecules using cpn10 and cpn60.

It can also be established that for mammalian cpn10's, there is a very close sequence homology. Thus, for example, the rat cpn10 molecule (Hartman et al., 1992, Proceedings of the National Academy of Sciences USA 89 3394-3398) has greater than 99% homology with the structure of bovine cpn10 reported in EMBL Data Base Directory under MT BTC PN10 which was submitted by J. E. Walker, MRC Lab. of Molecular Biology, Hills Road, Cambridge, UK. This has to be contrasted with bacterial cpn10's which have an average degree of homology with rat chaperonin 10 of only 34% (Hartman et al., 1992).

Early Pregnancy Factor (EPF)

EPF was first described as a pregnancy associated substance (Morton et al., 1976, Proc. R. Soc. B. 193 413-419) and its discovery created considerable interest as it enabled the detection of a potential pregnancy within 6-24 hours of fertilisation. Initially EPF was assigned a role as an immunosuppressant by virtue of its ability to release suppressor factors from lymphocytes (Rolfe et al., 1988, Clin. exp. Immunol. 73 219-225). These suppressor factors depress the delayed type hypersensitivity reaction in mice and therefore might suppress a possibly maternal immune response against the antigenically alien fetus. More recent studies have shown that production of EPF is not confined to pregnancy. It is a product of primary and neoplastic cell proliferation and under these conditions acts as a growth factor (Quinn et al., 1990, Clin. exp. Immunol. 80 100-108; Cancer Immunol. Immunother, 1992, 34 265-271). EPF is also a product of platelet activation and it is proposed therefore that it may play a part in wound healing and skin repair (Cavanagh et al., 1991, Journal Reproduction and Fertility 93, 355-365).

To date, the rosette inhibition test remains the only means of detecting EPF in complex biological mixtures (Morton et al., 1976, Proc R Soc B 413-419). This assay is dependent on the original finding of Bach and Antoine, 1968, Nature (Lond) 217 658-659 that an immunosuppressive antilymphocyte serum (ALS) can inhibit spontaneous rosette formation in vitro between lymphocytes and heterologous red blood cells. A modification of the assay was introduced to detect EPF after it was demonstrated that lymphocytes, preincubated in EPF, give a significantly higher rosette inhibition titre (RIT) with an ALS than do lymphocytes from the same donor without EPF as described in the 1976 reference above. This test has been described in detail in the above 1976 reference as well as in Morton et al., 1987, in "In Current Topics in Developmental Biology" Vol 23 73-92, Academic Press, San Diego, but briefly it involves a cascade of events with EPF binding to lymphocytes and sequentially inducing the release of suppressor factors (Rolfe et al., 1988, Clin. exp. Immunol. 73 219-225); (Rolfe et al., 1989, Immunol. Cell Biol. 67 205-208).

In Athanasas-Platsis et al., 1989, Journal Reproduction and Fertility 87 495-502 and Athanasas-Platsis et al., 1991, Journal Reproduction and Fertility 92 443-451, there is described the production of monoclonal and polyclonal antibodies to EPF and passive immunization of pregnant mice with these antibodies which causes loss of embryonic viability. These studies established that EPF is necessary for the successful establishment of pregnancy.

In Quinn et al., 1990, Clin. exp. Immunol. 80 100-108, it is proposed that EPF is a growth regulated product of cultured tumour and transformed cells. These cells are also dependent upon EPF for continued growth i.e. EPF acts in an autocrine mode.

It has been established that EPF plays a role in promoting tumour growth since the growth of tumour cells can be significantly retarded by anti-EPF mAbs. In addition this reference suggests that hybridomas producing high affinity anti-EPF antibodies may be inherently unstable.

In Quinn et al., 1992, Cancer Immunol. Immunother. 34 265-271, there is also described the effect of monoclonal antibodies (mAbs) to EPF on the in vivo growth of transplantable murine tumours. The main thrust of this reference is that neutralisation of EPF retards tumour growth in vivo.

It is clear from the above Quinn et al. 1992 reference that when cancer is in the very early stage of growth, neutralisation of EPF by anti-EPF mAb will prevent its development. However, once the cancer becomes established, treatment with these mAbs will retard but not entirely destroy the tumour.

Other references in regard to the role of EPF in tumour growth include Quinn, 1991, Immunol. Cell Biol. 69 1-6 and Quinn, K. A. in a PhD thesis entitled "Early pregnancy factor: a novel factor involved in cell proliferation" from the University of Queensland in Australia in 1991.

EPF is reviewed in detail by Morton et al., 1992, Early Pregnancy Factor, Seminars in Reproductive Endocrinology 10 72-82. The site and regulation of EPF production is described, followed by the purification of EPF from platelets and the relationship of the purified product to EPF derived from other sources. This review also discusses certain aspects of the bioassay for EPF (i.e. the rosette inhibition test) including monitoring purification procedures and investigating sources of production. The biological activity of EPF is discussed and possible clinical applications of EPF and its antagonists are described.

Morton et al., 1992, Reprod. Fertil Dev. 4 411-422 reviews previous publications describing the immuno suppressive and growth factor properties of EPF. The role of EPF in maintaining the pre-embryo is also discussed in this reference.

Both of the abovementioned references, which are essentially review articles, describe the preparation of purified EPF for blood platelets which included the initial sequential steps of heat extraction of the platelets, cation exchange chromatography on SP-Sephadex C-25, affinity chromatography on Heparin-Sepharose CL-6B and Concanavalin-A-Sepharose 4B. The final purification of EPF was achieved by high performance hydrophobic interaction chromatography, followed by three reversed phase (RP)-HPLC steps. After the final RP-HPLC step, EPF was isolated as single UV absorbing peak coincident with biological activity, well separated from a number of minor contaminants. The biological and radioactivity of an iodinated sample of this material eluted with identical retention time when fractionated under the same conditions. When analysed by SDS-PAGE and visualised by autoradiography, the iodinated material ran as a single band of approximate Mr 10,000, again coincident with biological activity. The approximate yield of EPF by this method was 5 µg per 100 platelet units.

This demonstrates that it was necessary to use this complex purification procedure to obtain only a small amount of native EPF and thus this method could not be used on a commercial scale. In this regard, the only practical sources known for obtaining native EPF at this time were platelets and regenerating liver.

Surprisingly, in accordance with the present invention, the final fractionated EPF when subjected to sequencing as more fully described hereinafter found that the structure of native EPF corresponded to chaperonin 10 which could not have been predicted from the aforementioned prior art.

This unexpected discovery as will be apparent from the disclosure hereinafter has now been reduced to practice in that antibodies to recombinant chaperonin 10, as described hereinafter as well as derivatives or fragments thereof, has been found to have all the biological activity previously associated with antibodies to EPF. EPF can now be produced commercially which was not the case previously using suitable techniques for producing recombinant cpn10 or producing cpn10 synthetically. It will thus be apparent that this will also facilitate commercial production of antibodies to cpn10.

SUMMARY OF THE INVENTION

In one aspect, the invention provides for the production of antibodies specific for recombinant cpn10 having the amino acid sequence as hereinafter described as well as derivatives or fragments thereof.

Another aspect of the invention is the use of such antibodies. The use of the antibodies includes cellular growth suppressing activity or an immune enhancing activity.

The present invention includes within its scope the use of monoclonal and/or polyclonal antibodies to the recombinant cpn10 as hereinafter described as well as fragments or derivatives thereof.

EXPERIMENTAL

A. PURIFICATION OF CPN10 AND ANTIBODY PRODUCTION (i) Purification of Human EPF from Human Blood Platelets (FIGS. 1a. 1b, 1c, 1d)

Extraction

Platelet concentrates (from the Blood Bank), up to 7 days clinically outdated, were washed with Tyrodes buffer, following the techniques described in Methods in Enzymology, 1989, 169 7-11, snap frozen in liquid $N_2$ and stored at −70° C.

Immediately prior to purification, approximately 100 washed platelet units were thawed in a boiling water bath, then held at 75-85° C. for 15 min with continuous, gentle stirring. After cooling on ice, cellular debris was removed by centrifugation (8000 g, 20 min, 4° C.) and the pellet extracted twice by homogenisation in 0.05 M-acetic acid/0.1 M-NaCl/0.1 mg/ml sodium azide pH 3.0 followed by centrifugation (8 000 g, 15 min 4° C.). The three supernatants were pooled giving a total extract volume of 500-600 ml.

Ion-Exchange Chromatography

This extract from 100 platelet units was adjusted to pH 3.0 with conc. HCl and stirred gently, overnight, 4° C., with 250 ml SP-Sephadex C-25 (Pharmacia-LKB), previously swollen and equilibrated with 0.05 M-acetic acid/0.1 M-NaCl pH 3.0. The gel was then packed into a column washed with 20 vol of the same buffer and eluted with 5 vol 0.5 M-sodium phosphate buffer/0.05 M-NaCl pH 7.5. The gel was then discarded.

Affinity Chromatography

The SP-Sephadex eluate was adjusted to pH 6.3-6.4 with conc. HCl and applied to a column of Heparin-Sepharose CL-6B (2.5×7.5 cm; Pharmacia-LKB) previously equilibrated with 0.05 M-sodium phosphate buffer/0.05 M-NaCl pH 6.3. The column was then washed with 5 vol of the same buffer and eluted with 5 vol 0.05 M-Tris-HCl/5 mM-CaCl$_2$/0.2 M-NaCl pH 7.5, applied in the reverse direction to that used for sample application.

High Performance Hydrophobic Interaction Chromatography (HIC-h.p.l.c.)

Solid (NH$_4$)$_2$SO$_4$ was added to the Heparin-Sepharose eluate to a final concentration of 2 M and, after passage through an 0.45 μm filter, the sample was pumped through a dedicated solvent line onto a TSK Phenyl 5PW column (7.5×75 mm, Pharmacia-LKB), previously equilibrated with 0.1 M-Tris-HCl pH 7.0/5 mM CaCl$_2$/2 M-(NH$_4$)$_2$SO$_4$. The column was washed with 10 vol of the same buffer and eluted with a 50 min linear gradient from this buffer to 0.1 M-Tris-HCl pH 7.0/5 mM-CaCl$_2$/10% acetonitrile. (FIG. 1a)

RP-h.p.l.c.-1

Figure 1B:
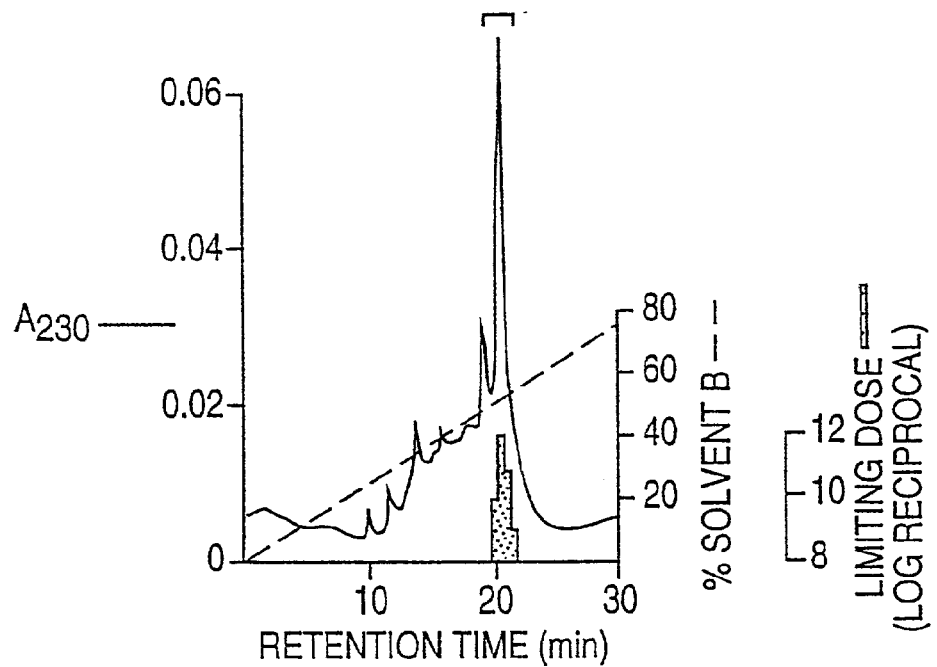

Active HIC-h.p.l.c. fractions were pooled, then fractionated on a C$_3$ column (Ultrapore RPSC, Beckman Instruments) using a solvent system consisting of A, 0.04 M Tris/HCl pH 7.0/5 mM-CaCl$_2$ and B, 0.04 M-Tris/HCl pH 7.0/5 mM-CaCl$_2$/80% (v/v) acetonitrile. The column was equilibrated with Solvent A prior to sample application, after which it was washed with 5 vol solvent A and eluted with a 30 min linear gradient from this solvent to 75% solvent B. (FIG. 1b)

RP-h.p.l.c.2

Figure 1C:
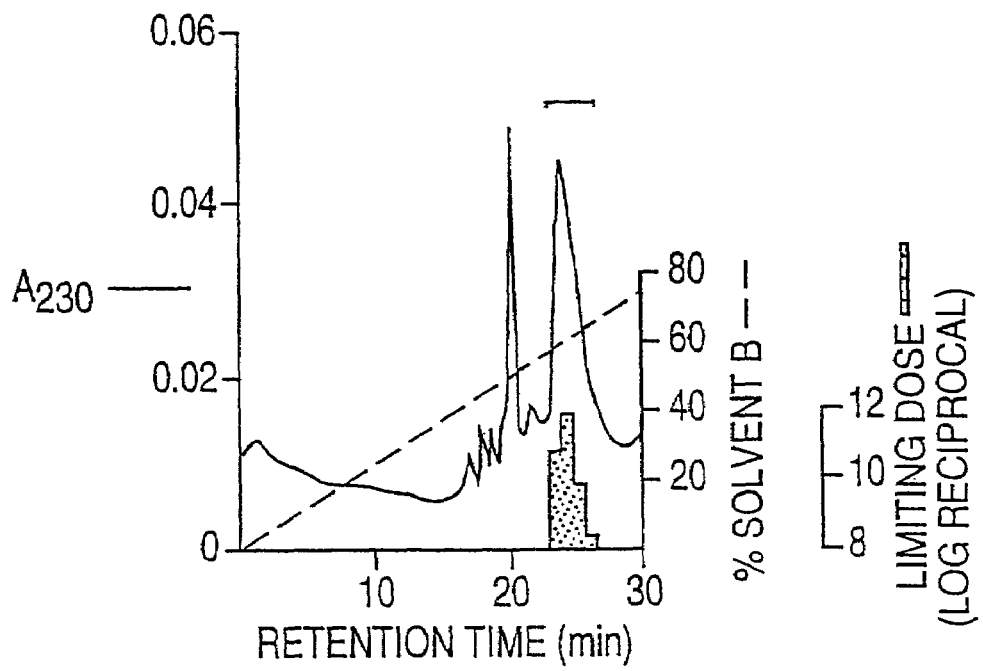

Active fractions from RP-h.p.l.c.-1 of several 100 unit platelet preparations were pooled, EDTA and DTT added to a final concentration of 20 mM and 1 mM respectively and the mixture allowed to stand for 0.5-1 h, 4° C. Following dilution with 2 vol solvent A, it was applied to a C$_3$ column, dedicated to this and subsequent steps, and fractionated as described for RP-h.p.l.c.-1, but omitting CaCl$_2$. (FIG. 1c)

Rph.p.l.c.3

Figure 1D:
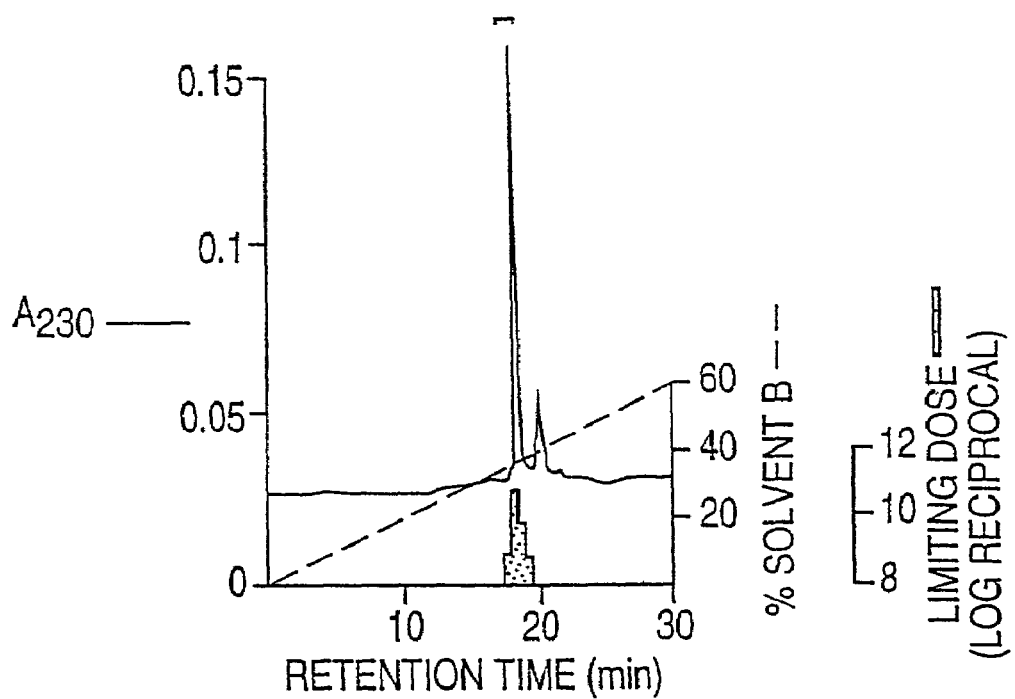

Active fractions from RP-h.p.l.c.-2 were pooled, trifluoroacetic acid (TFA) added to a final concentration of 0.1% and, following dilution with 2 vol 0.1% TFA, the mixture was applied to the C$_3$ column, which had been equilibrated previously with 0.1% TFA. The column was then eluted with a 30 min linear gradient from this solvent to 60% (v/v) acetonitrile/0.1% TFA, followed by a 3 min linear gradient to 90% (v/v) acetonitrile/0.1% TFA. Active fractions were pooled. (FIG. 1d)

One unit represents platelets from a single blood donation which is approximately 500 ml. The "active fractions" were fractions active in the rosette inhibition test.

Purification of EPF from Other Sources

The purification of cpn10 from various sources have been summarised in Cavanagh et al., 1994, Eur. J. Biochem. 222 551-560.

Biological activity followed the same pattern throughout the complex purification scheme described above for human platelets. Furthermore the final active fraction from all sources was bound specifically by an immobilised monoclonal anti-EPF and could be recovered virtually quantitatively (see FIG. 1e).

These studies are important for several reasons:

A. The biochemical and immunological similarity observed with all these materials provides strong evidence that the bioassay is detecting a single substance or closely related family of substances acting in diverse biological situations.

B. The active agents purified from all of these materials are from several to many orders of magnitude more potent than virtually all of the substances previously reported to be EPF summarised in the abovementioned Morton et al., 1992 reference. This confirms our surmise, based on detailed analysis of the EPF bioassay as discussed above, that activity associated with most putative EPF preparations must reflect the presence of a very minor contaminant.

C. The only source materials providing sufficient EPF to study at the protein (as opposed to activity) level were platelets and regenerating liver, yielding, respectively, an average of 15 μg per 100 units (equivalent to ~50 liter blood) and 5 μg per 40 g tissue (liver remnant from 6 rats). It is immediately apparent that far more EPF is present within the cell than appears in the extracellular space; nevertheless, accumulated knowledge of the biology of EPF (reviewed recently in the abovementioned Morton et al. 1992 reference) indicates that this extracellular appearance is not fortuitous.

Human platelet-derived EPF, being most abundant, has been studied in some detail. On SDS-PAGE, it ran as a single band of M$_r$ approx, 8 500, coincident with biological activity (see FIG. 2a); EPF from regenerating rat liver exhibited identical behaviour. Mass spectometry of the platelet material provided an accurate and precise determination of molecular mass 10 843.5±2 Da, along with definitive evidence of the high degree of homogeneity of the preparation (see FIG. 2b). Following attempts at Edman degradation, which indicated that the molecule is N-blocked, proteolytic cleavage of approx. 4 nmol EPF was undertaken. Resultant peptide fragments were separated by reversed-phase HPLC and subjected to sequencing by Edman degradation. Three areas of sequences containing 12 (fragment 1, SEQ ID NO:22), 27 (fragment 2, SEQ ID NO:23) and 33 (fragment 3, SEQ ID NO:24) residues were found to correspond with residues 7 to 18, 27-53 and 69-101 (the C-terminus) in rat mitochondrial cpn10. In fragment 2, residue 52 was different (S in cpn10, G in rat cpn10; this change alone could account for human cpn10 being 30 Da larger than rat cpn10). All other residues were identical, consistent with the highly conserved nature of chaperonins (see FIG. 2c).

Since confirming sequence identity between EPF and cpn10, several studies of functional relationship have been performed, using rat mitochondrial cpn10. E. coli cpn10 (known as groES) and E. coli cpn60 (groEL). First it has been demonstrated that cpn10 can act as EPF. Rat cpn10 was tested in the EPF bioassay and found to be positive over the range of dilutions expected: this activity could be neutralised by monoclonal antibodies to EPF. Interestingly, E. coli cpn10, which is ~40% homologous with rat cpn10. exhibited no activity in the bioassay. This is consistent with the observation that E. coli conditioned medium is not active in the EPF bioassay, while medium conditioned by all mammalian cell lines tested, as well as by yeast cells is active. Cpn60 was inactive in the bioassay and had no effect upon the activity of EPF. It was then shown that EPF can act as cpn10. EPF was mixed with cpn60. in the presence or absence of ATP, and the mixture fractionated on a TSK G3000SW gel permeation column; resultant fractions were analysed by SDS-PAGE. Cpn60 is a decatetramer and elutes in the excluded volume of this column (exclusion limit 300 000). In the presence of ATP, but not in its absence, EPF also appears in this fraction, demonstrating formation of a stable complex with cpn60. This fraction was active in the EPF bioassay but the equivalent fraction from the experiment without ATP (where EPF did not associate with cpn60) was not (see FIG. 3a). Thus EPF and cpn10 activity reside in the same molecule.

Figure 3B:
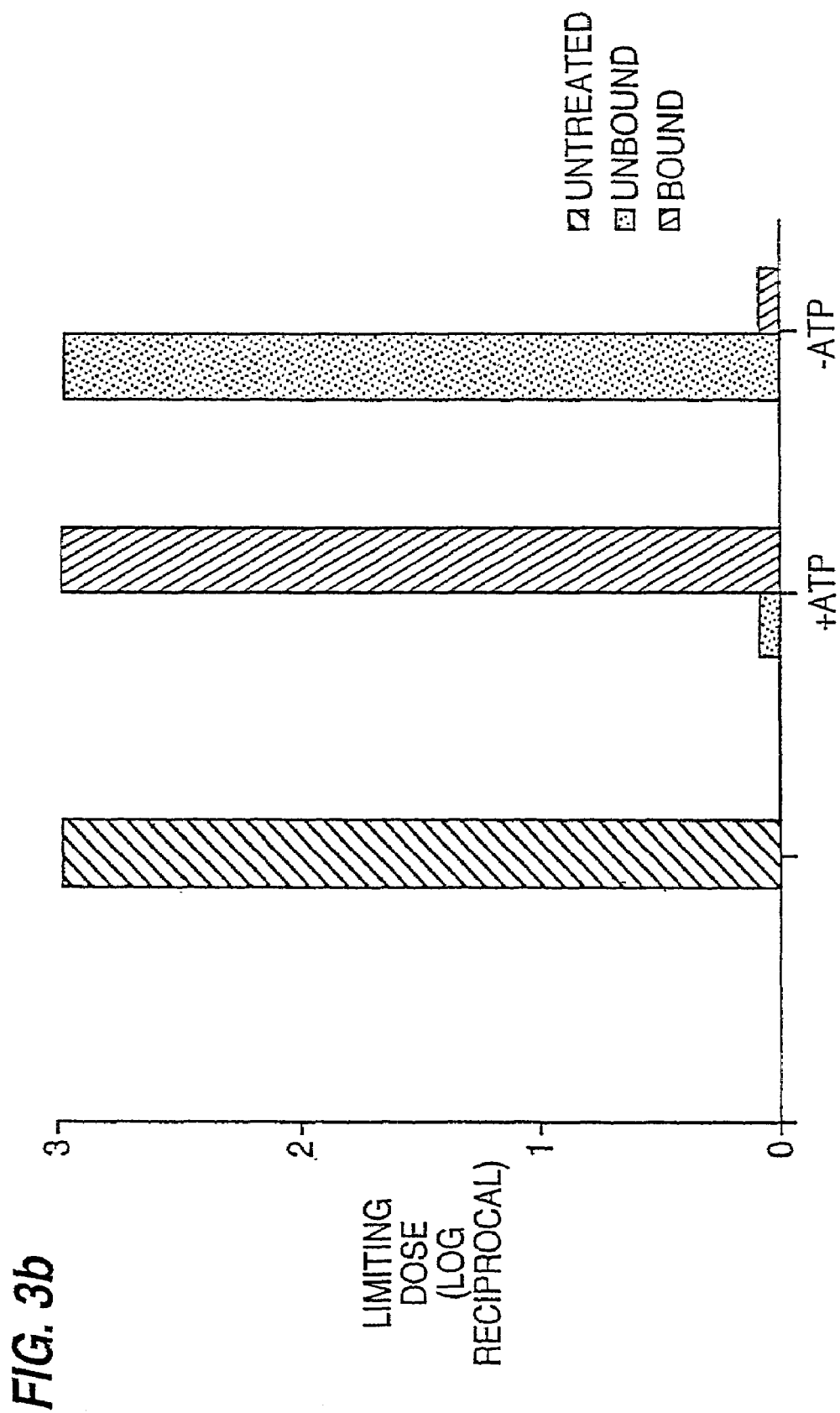

These investigations provide unequivocal evidence that platelet-derived EPF is a structural and functional homologue of cpn10; the relationship between cpn10 and activity in the rosette inhibition test was then examined (FIG. 3b). In the presence, but not in the absence of ATP, immobilised cpn60 could remove all activity from the archetypal source material, pregnancy serum and activity could be recovered by removing ATP from the immobilised complex. As with the experiment described in FIG. 3a, this requirement for ATP demonstrates the specificity of the interaction between cpn60 and the active moiety; cpn10 is thus the molecular entity initiating response in the EPF bioassay.

Identification of EPF as a cpn10 has been a major step forward in research on this subject and helps to explain many of the findings that have been made to date. Criticism has been raised against claims that EPF production occurs in such a wide variety of biological situations e.g. pre-and post-implantation pregnancy, primary and tumour cell proliferation and platelet activation. In its role as a hsp (heat stress protein) following the advent of the present invention, these are all conditions in which the rapid onset of EPF production would now be expected. Functions of hsp's that are vital to the survival of cells are intracellular as shown in the Linquist et al. reference above. In contrast, the activity of EPF described to date is extracellular; for example, it appears in serum of mice within 4 to 6 hours after mating as discussed in Morton et al., 1987, Current Topics in Development Biology, Vol 23 73-92 and 4 to 8 hours after partial hepatectomy in rats as shown in the Quinn PhD thesis (1991). We have shown that EPF can act in an autocrine mode as discussed in the Quinn et al., 1990 reference referred to above or exocrine mode as discussed in the Rolfe et al. 1988 referred to above: these are not roles previously described for hsp's.

It will also be appreciated that since the structure of EPF is now known, it can be produced in commercial quantities by any suitable technique such as by recombinant DNA techniques or by chemical synthesis.

(ii) Production of Anti-cpn10-Derived Peptide

Described here are the methods used and results encountered in the production of anti-cpn10-derived peptide. Peptides of cpn10 may include the following amino acid sequences (SEQ ID NOS: 1-12);

```
(i)       AGQAFRKFLPL;
(ii)      Ac-AGQAFRKFLPL:
(iii)     EKSQGKVLQAT
(iv)      A₁AGQAFRKFLPLA₂,;
(v)       AGQAFRKFLPLA₂.
(vi)      A₁AGQAFRKFLPL:
(vii)     Ac-A₁AGQAFRKFLPLA₂;
(viii)    Ac-AGQAFRKFLPLA₂;
(ix)      Ac-A₁AGQAFRKFLPL;
(x)       A₁EKSQGKVLQATA₂;
(xi)      EKSQGKVLQATA,;
(xii)     A₁KSQGKVLQAT;
``` wherein $A_1$ and $A_2$ are amino acid sequences which may be added to one or each end of molecules (i) through (xii) and Ac is acetyl.

Anti-cpn10-derived peptides antibodies may include antibodies raised against any one of the aforementioned amino acid sequences (i)-(xii). As an example, antibodies have been raised against an N-terminal fragment (Ac-AGQAFRKFLPL, SEQ ID NO:2) and an internal fragment (EKSQGKVLQAT, SEQ ID NO:3).

It will be appreciated in the abovementioned peptides that such peptides may include a single amino acid addition, deletion or substitution and the invention also includes antibodies raised against such peptides.

Methods

Synthesis of cpn10 Derived Peptides

Peptides were synthesized to correspond with an N-terminal fragment (N-peptide i.e. Ac-AGQAFRKFLPL, SEQ ID NO:2) and an internal fragment (I-peptide i.e. EKSQGKVLQAT, SEQ ID NO:3).

Conjugation of Peptides to Ovalbumin

Peptides were conjugated to ovalbumin by the heterobifunctional reagent SPDP, following manufacturer's instructions (Pharmacia-LKB Biotechnology, Uppsala, Sweden).

Immunisation Schedules

Adult outbred New Zealand rabbits were immunised with one of the conjugates in 4× weekly injections followed by several monthly boosts.

For injection, the antigen was dialysed into 0.9% saline (Mr 12-15000 cut off dialysis tubing, Visking, Union Carbide, Ill., USA) and emulsified with an equal volume of Freund's adjuvant (complete for the first injection, incomplete thereafter). Immunisations were via the s.c. route. Table 1 shows the amount of antigen injected.

Screening of Antiserum

Antisera were tested in an ELISA against the relevant antigens (viz. I-peptide or N-peptide: ovalbumin) (5 mg/ml). Bound IgG was detected by the biotin-streptavidin system (Amersham) with o-phenylene diamine as substrate. Absorbance was read at 492 nm.

Anti-N-peptide Abs were also tested in parallel with anti-EPF Abs #810 and #816 (Athanasis-Platsis et al., 1989, J. Reprod. Fert. 87 495-502) against platelet derived EPF (1 mg/ml) (Cavanagh et al., 1994, Eur. J. Biochem. 222 551-560) and N-peptide (5 mg/ml).

Purification of Antibodies

IgG was purified from serum by affinity chromatography. N and I peptides, and ovalbumin were coupled separately to a HiTrap™ affinity column (HiTrap NHS-activated 1 ml, Pharmacia-LKB) following the manufacturer's instructions. Each column was equilibrated with 0.05 NaPi-0.5M NaCl, pH 7.4, and the relevant antiserum applied, according to the manufacturer's instructions. After extensive washing with equilibration buffer, bound rabbit IgG was eluted by 0.2M glycine. pH 2.5. The pH of the eluate was adjusted with 2M Tris To approximately 7.4.

The purity of the Abs in the eluted fractions was determined by SDS-PAGE, then the strongest fractions pooled.

Protein Estimation

Protein (IgG) was determined by the method of Lowry (Lowry et al., 1951, J. Biol. Chem. 193 265-275), using a commercial preparation of Folin and Ciocalteu's reagent (Stansens, Qld, Australia). The standard curve was constructed with a purified rabbit IgG preparation (20 mg/ml; Silenus, Hawthorne, Australia).

Results

The ELISA screening of the antibodies provided some interesting results.

Figure 4C:
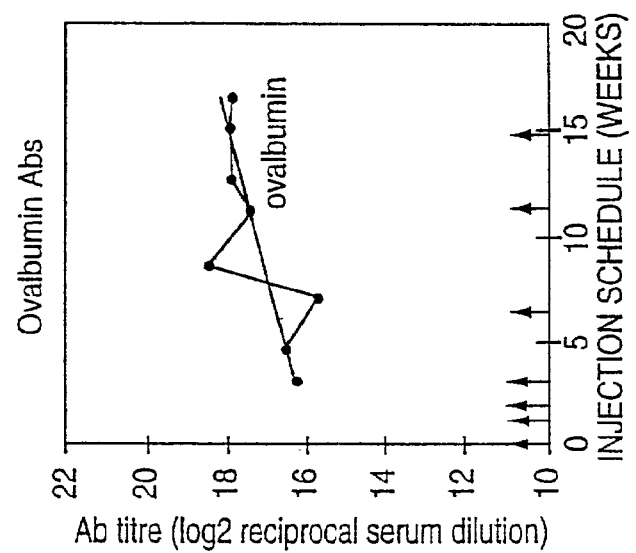

The anti-peptides Abs titre decreased even with repeated boosting (FIGS. 4a, 4b), while the production of anti-ovalbumin control Abs gave a normal response (FIG. 4c). Note that the titre of anti-ovalbumin Abs in rabbits immunised with the peptide conjugates (FIGS. 4a, 4b) decreased as well.

Cross reactivity studies are shown in FIG. 5.

The "anti-EPF #810" and "anti-EPF #816" antibodies are typical prior art anti-EPF antibodies disclosed in Athanasis-Platsis et al, (1989), Supra. Such prior art antibodies being IgG polyclonel antibodies are low affinity antibodies as shown in FIG. 5 when compared to high affinity antibodies of the invention exemplified by the anti-N peptide antibody.

The titre of affinity purified Abs was determined by ELISA against the immunising peptide conjugated to bovine serum albumin (BSA). This test also demonstrated the efficiency of the procedure. Results are shown in Table 2.

These Ab preparations were shown in SDS-polyacrylamide gel electrophoresis to be approximately 95% pure.

Conclusion

The decreasing titre of Abs during the immunising schedule suggests a role for cpn10 in the proliferation of B cell clones. The instability of antibody-producing B cell clones which produce anti-EPF antibodies has been previously described. The pattern of anti-EPF antibody production was as described above, with maximum titres obtained 5 weeks after the initial immunisation and then falling despite frequent boosting. In vitro, hybridomas producing anti-EPF antibodies were inherently unstable (Quinn et al., 1990, Clin. Exp. Immunol. 80 100-108). The difficulty in making a stable cell line of a hybridoma which produces an anti-EPF/cpn10 antibody may be due to the autocrine action of EPF/cpn10 in cell proliferation, i.e. antibodies neutralize EPF/cpn10 which proliferating cells produce for their own growth advantage.

(iii) PREPARATION OF ANTIBODIES TO RECOMINBANT CPN10

Cloning of Human cDNA Encoding cpn10 and Production of cpn10

Production for commercial use may be obtained by inserting a mammalian cpn10 gene, preferably a human cDNA cpn10 gene, into a suitable vector such as plasmids from the pGEX system, and pET system expressing the encoded mammalian cpn10 and purifying the recombinant cpn10.

| Abbreviations | |
| --- | --- |
| ANGIS | Australian National Genomic Information Service |
| bp | base pair |
| BSA | bovine serum albumin |
| cDNA | complementary DNA |
| cpn10 | Chaperonin 10 |
| DNA | deoxyribonucleic acid |
| E. coli | Escherichia coli |
| GSH | glutathione (reduced form) |
| GST | glutathione-S-transferase |
| LB | Luria-Bertani Broth |
| M | Molar |
| ORF | open reading frame |
| PCR | polymerase chain reaction |
| rEPF | recombinant Early Pregnancy Factor |
| RSP | reverse sequencing primer |
| SDS | sodium dodecyl sulphate |
| SDS-PAGE | sodium dodecyl sulphate-polyacrylamide gel electrophoresis |
| Tris | Tris(hydroxymethyl)aminomethane |
| USP | universal sequencing primer |

Materials and Methods

Cloning of Human cpn10 Open Reading Frame

Ploymerase chain reaction (PCR) was used to initially amplify part of the ORF (274 bp) of the human cpn10 cDNA from a melanoma cell line A2058 cDNA lambda library (Stratagene). A degenerate cpn10 amplimer (P1) was designed from the amino acid sequence VLDDKDYFL (SEQ ID NO:15) corresponding to amino acid residues 83-91 of human cpn 10. The primer P1 has the sequence 5' ARRAARTARTCYTTRTCRTC 3' (SEQ ID NO:16) where R is A or G and Y is C or T. The reverse sequencing primer (RSP) was used for sequencing DNA constructs and has the sequence 5' CAGGAAACAGCTATGAC 3' (SEQ ID NO:17). The universal sequencing primer has the sequence 5' GTAAAACGACGGCCAGT 3' (SEQ ID NO:18). PCR amplification of the page library was achieved using a non-specific upstream amplimer (RSP) and P1 each at 0.5 µM final concentration, 1.5 mM MgCl$_2$ (Pharmacia Biotech), 1×polymerase buffer (Bohringer Mannheim) and 5 units of Thermus aquaticus DNA polymerase (Boehringer Mannheim) in a final volume of 50 µL. For 30 cycles, the parameters were: denaturation at 94° C. for 1 mm. annealing at 40° C. for 30 sec and extension at 72° C. for 3 mm. A final extension at 72° C. for 7 min was follwed by a soak cycle at 4° C. for 10 min. An aliquot of 1 µL was reamplified under the same conditions to increase the copy number.

Two cpn10 specific amplimers encompassing the open reading frame were designed. The upstream primer P2, 5'-GCGCGGATCCATGGCAGGACAAGCGTTTAG-3' (SEQ ID NO:19), was designed from the sequence of the initial PCR fragment. The downstream primer P3, 5'-ATAT-GAATTCAGTCTACGTACTTTCC-3' (SEQ ID NO:20) was designed from sequence from obtained from the Expressed Sequence Tag database via ANGIS (Accession No. HUM00TB037). A 319 bp fragment was amplified from the phage library using the same reaction and cycling conditions as above except the annealing temperature was 50° C.

DNA Constructs and Analysis

Figure 6A:
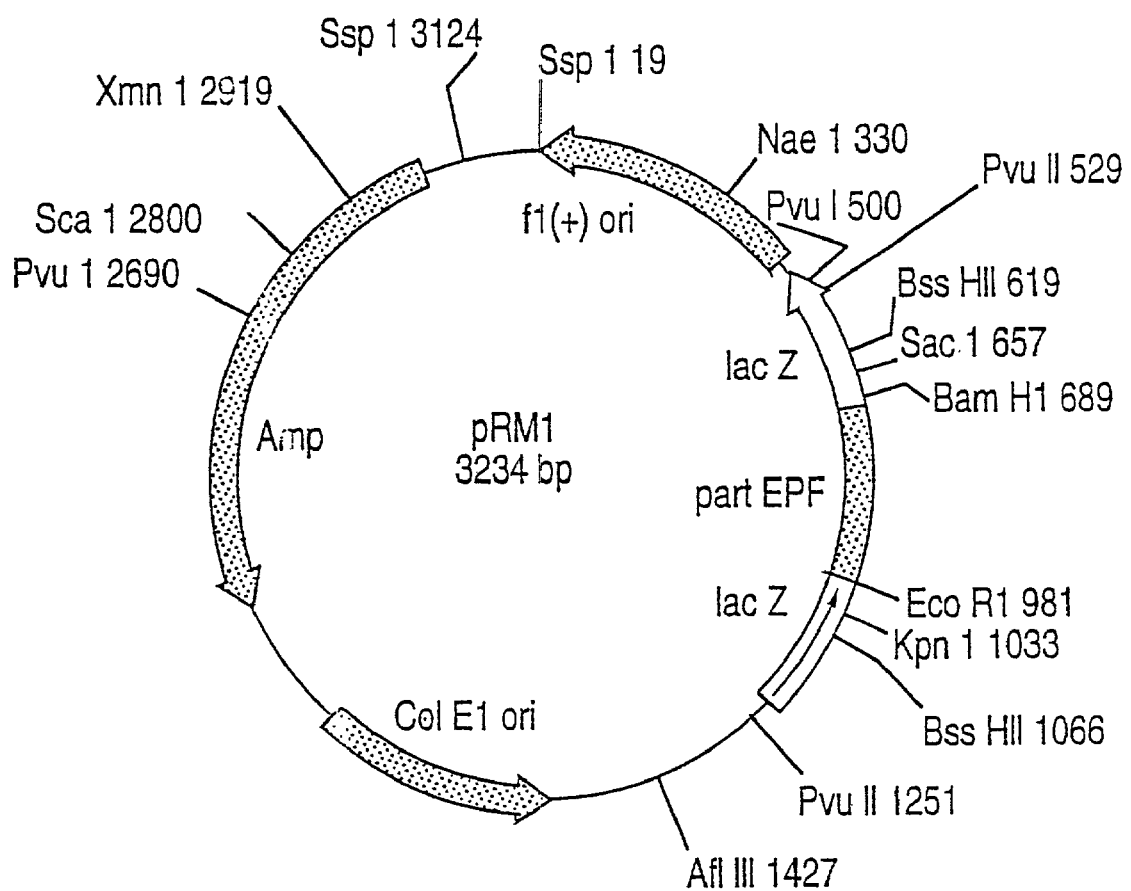
Figure 6B:
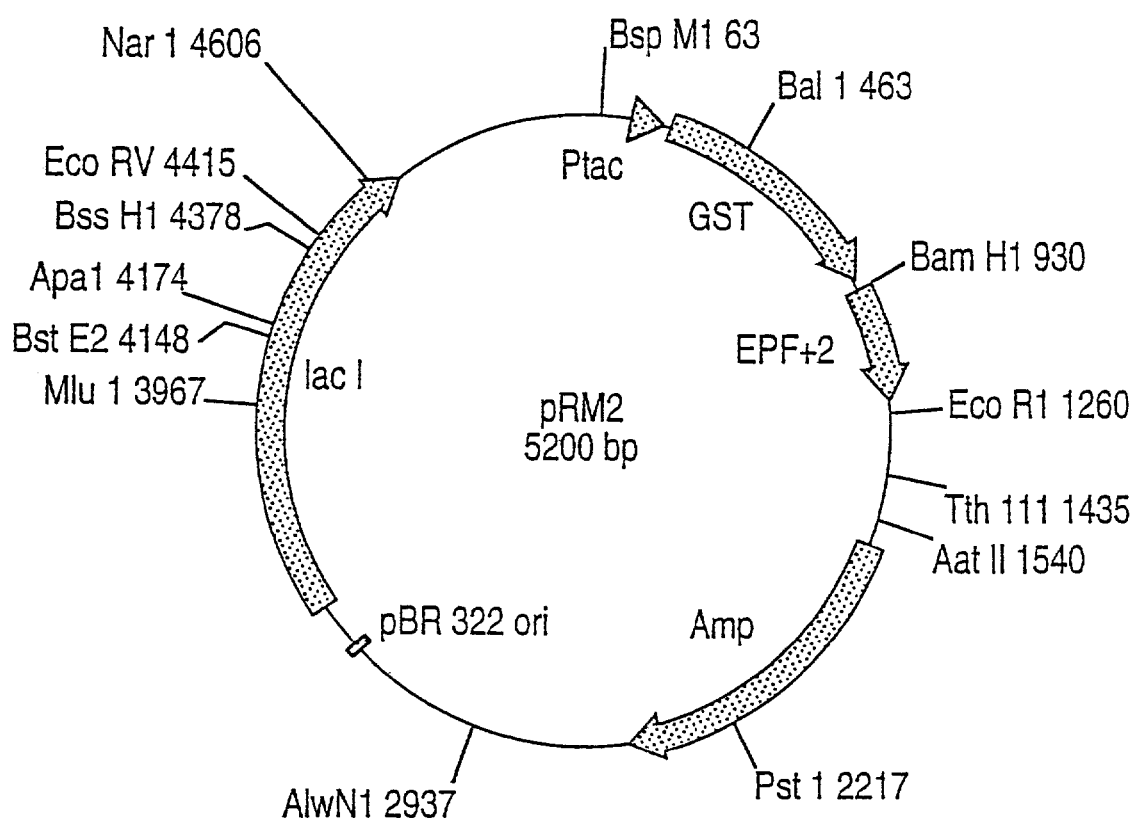
Figure 6C:
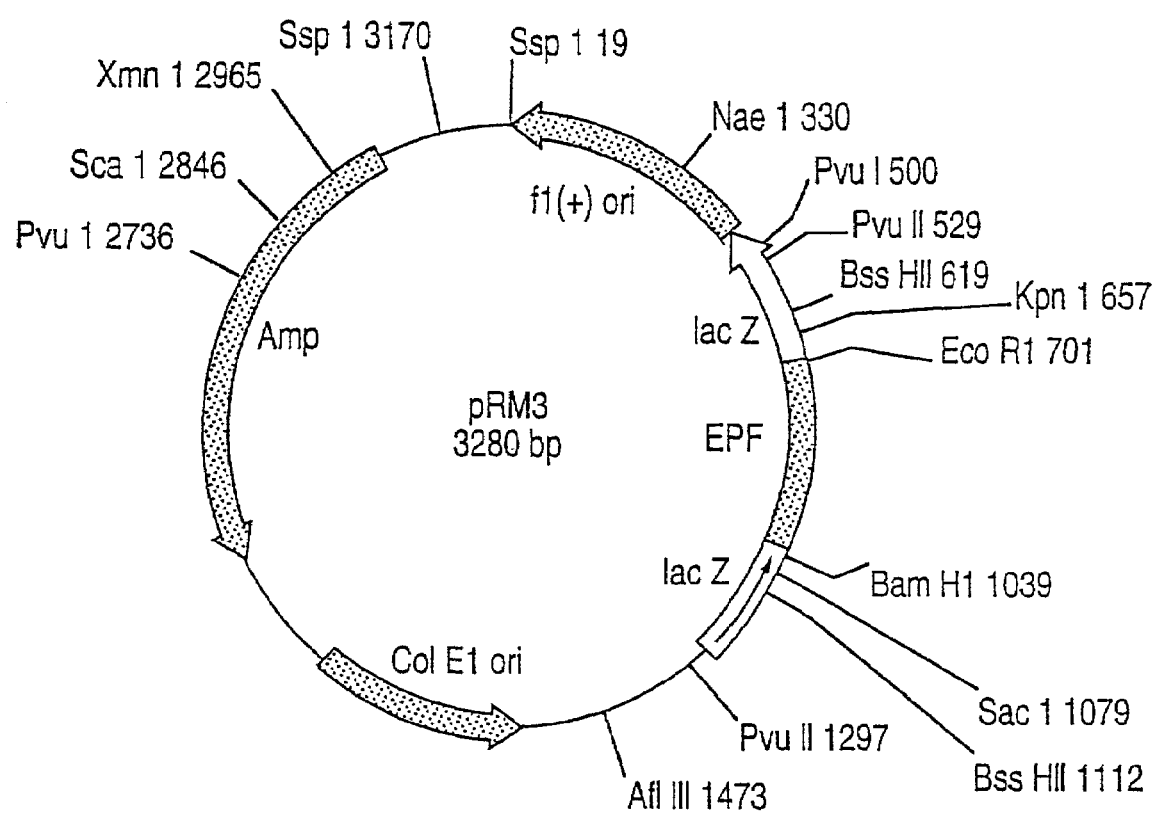

All restriction enzyme digests of PCR products and vectors were performed according to Sambrook et al. (Sambrook et al., 1989, Molecular Cloning: A Laboratory Manual. 2nd Ed. Cold Spring Harbor Press, Cold Spring Harbor, N.Y.) using restriction enzymes and their buffers obtained from Boehringer Mannheim. The initial PCR fragment was digested with Eco R1 and ligated (Sambrook et al., 1989, Molecular Cloning: A Laboratory Manual. 2nd Ed. Cold Spring Harbor Press, Cold Spring Harbor, N.Y.) into the Eco R1 and Sma I sites of pBluescript KS(+) (Stratagene) creating the plasmid pRM1 (FIG. 6a; partial cpn10 insert 274 bp). The 319 bp product was digested with Bam HI and Eco R1 and initially cloned into the expression plasmid pGEX-2T (Pharmacia Biotech) creating the plasmid pRM2 (FIG. 6b). To confirm its identity, the Bam HI-Eco R1 fragment was subcloned into pBluescript (SK+) (pRM3; FIG. 6c) and sequenced. DNA was analysed on 0.8-1.0% (w/v) agarose gels containing ethidium bromide and after electrophoresis was viewed under UV illumination.

Transformation of E. coli

Competent E. coli DH5α cells (100 μL) were transformed with the plasmids by the heat pulse method (Sambrook et al., 1989, Molecular Cloning: A Laboratory Manual. 2nd Ed. Cold Spring Harbor Press, Cold Spring Harbor, N.Y.). The mixture of cells and DNA (10-100 ng) was placed on ice for 30 min and heat pulsed for exactly 2 min at 42° C. and placed back on ice for 2 min. The cells were allowed to recover at 37° C. with shaking for 1 hr after the addition of 0.9 mL of LB. A 100 μL aliquot was plated onto LB agar plates supplemented with Ampicillin at a final concentration of 100 μg/mL. After incubation overnight at 37° C., random colonies were selected for further investigation.

DNA Sequence Determination

Restriction fragments of the PCR products were cloned into pBluescript and sequenced in both orientations by the dideoxy chain-termination method using the T7 Polymerase Kit according to the manufacturer's instructions (Pharmacia Biotech). Approximately 2 μg of plasmid DNA was denatured, ethanol precipitated and annealed to either the USP, RSP or P3. The sequencing reactions were electrophoresed on a 8% acrylamide/46% urea gel. After fixing and drying, X-ray film was exposed to the gel overnight and developed.

Expression and Purification of Recombinant cpn10 in E. coli

Clones transformed with pRM2 were screened for expression of the Glutathione-S-transferase fusion protein on a small culture scale (2 ml) according to methods described by Smith et al. (Smith et al., 1988, Gene 67 (1) 31-40). An overnight culture was diluted, induced to express the fusion protein by the addition of IPTG to 0.1 mM and grown at 37° C. for several hours. The cells were pelleted, lysed in PBS/0.1% Triton X-100 and the lysate mixed with 50% Glutathione-Agarose beads (Sigma Chemical Company). The recombinant fusion protein was eluted from the affinity beads by boiling in SDS loading buffer. An aliquot of the sample was run on a 10% SDS-PAGE gel. The gel was fixed and then stained with Coomassie blue. After confirming the expression of the fusion protein the purification of rcpn10 from the GST moiety was undertaken on a larger scale.

Cells were grown and induced as above, the cell pellet resuspended in PBS, sonicated (output level 4, 50% duty cycle, 2×30 sec) and the cell lysate stored at −30° C. Lysate from 10 liter cell culture was thawed and rcpn10 isolated by similar techniques to those used by Gearing et al. (Gearing et al., 1989, Biotechnology 7 1157-1161) for isolation of rLIF. Briefly, Triton X-100 was added to a final concentration of 0.1% and cellular debris removed by centrifugation (15 min. 15000 rpm, 4° C.). Ten ml glutathione-Sepharose 4 B gel (Pharmacia—LKB Biotechnology) was added to the supernatant and the slurry mixed for 2 hr, 4° C. The gel was pelleted, washed×5 with 50 ml PBS/0.1% Triton X-100 once with 50 ml 0.05 M Tris-HCl pH 8.0/0.15 M NaCl and once with 0.05M Tris-HCl pH 8.0/0.15 M NaCl/2.5 mM CaCl$_2$. The gel was resuspended in 4 ml of 0.05 M Tris-HCl pH 8.0/0.15 M NaCl/2.5 mM CaCl$_2$ buffer, 1000 units thrombin (Sigma T6884) added and the slurry was mixed in a shaking waterbath for 1 hr, 37° C. The gel was pelleted, the supernatant retained, and the gel was then washed with 3×4 ml 0.05 M Tris-HCl pH 8.0/0.15 M NaCl. These washes and the first supernatant, which contain the rcpn10, were pooled, yielding 4-5 mg recombinant protein. Additional rcpn10, which was non-specifically bound to the gel, was recovered as follows. Four ml 0.05 M Tris-HCl pH 8.0/2 M NaCl was added and the slurry mixed for 2 hr, 4° C.

After pelleting, the gel was washed with 3×2 ml of this 0.05 M Tris-HCl pH 8.0/2 M NaCl buffer, the washes pooled with the first supernatant, yielding a further approximately 1 mg rcpn10. Protein concentrations were estimated by the method of Lowry et al. (Lowry et al., 1951, J. Biol. Chem. 193 265-275); proteins were analysed by SDS-PAGE using 15% Tris-Tricine gels (Schagger et al., 1987, Anal. Biochem. 166 368-379).

The recombinant cpn10 has two additional amino acids at the N terminus. The N terminus of the recombinant protein is Gly-Ser-Methionine-ala whereas the N-terminus of native protein is Ac-ala. The amino acid sequence (SEQ ID NO:21) of the recombinant cpn10 is as follows:

GSMAGQAFRKFLPLFDRVLVERSAAETVTKGGIMLPEKSQGKVLQATVE

AVGSGSKGKGGEIQPVSVKEGDKVLLPEYGGTKVVDDKDYFLFRDGDI

LGKYVD.

Antibodies were raised against the GST:rcpn10 fusion protein.

Figure 7:
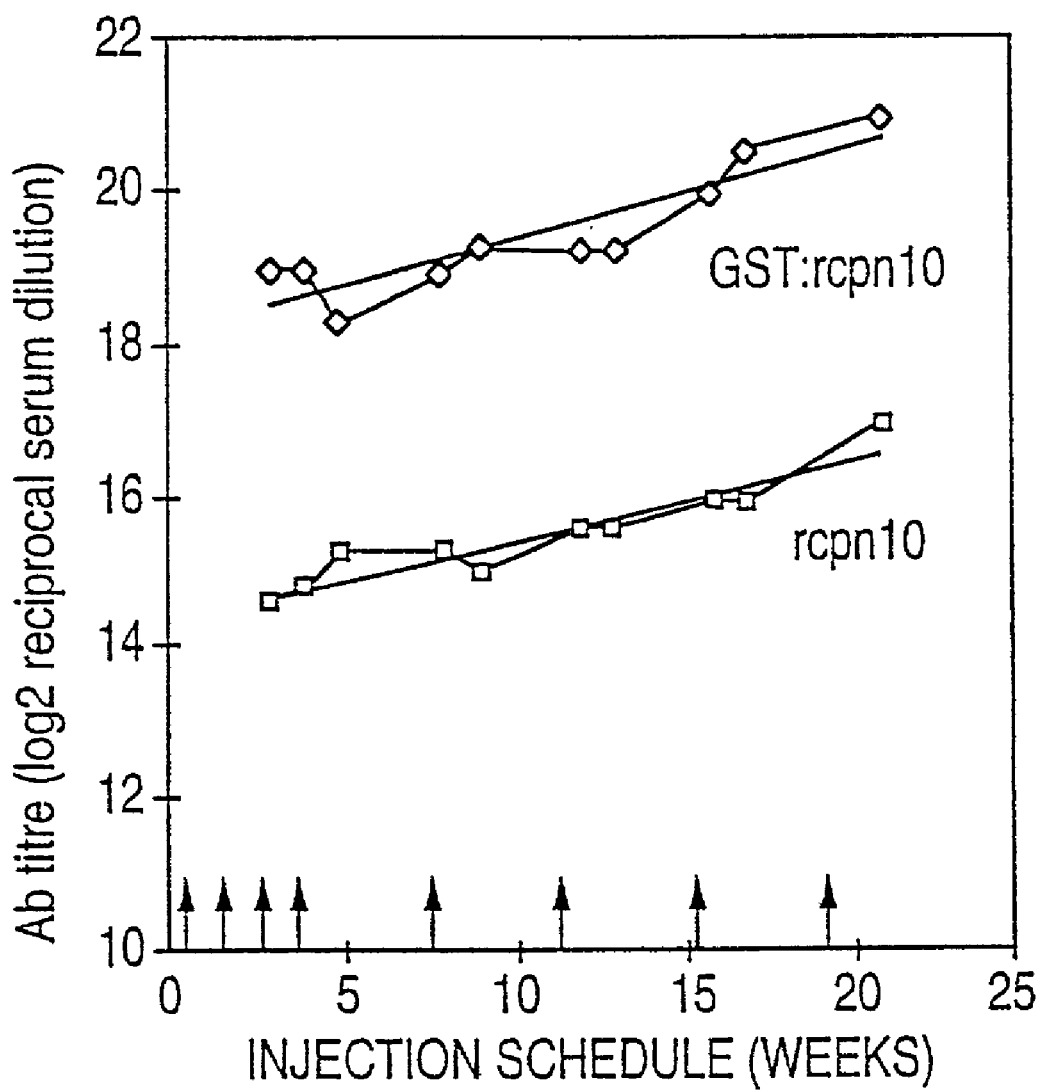
Figure 8:
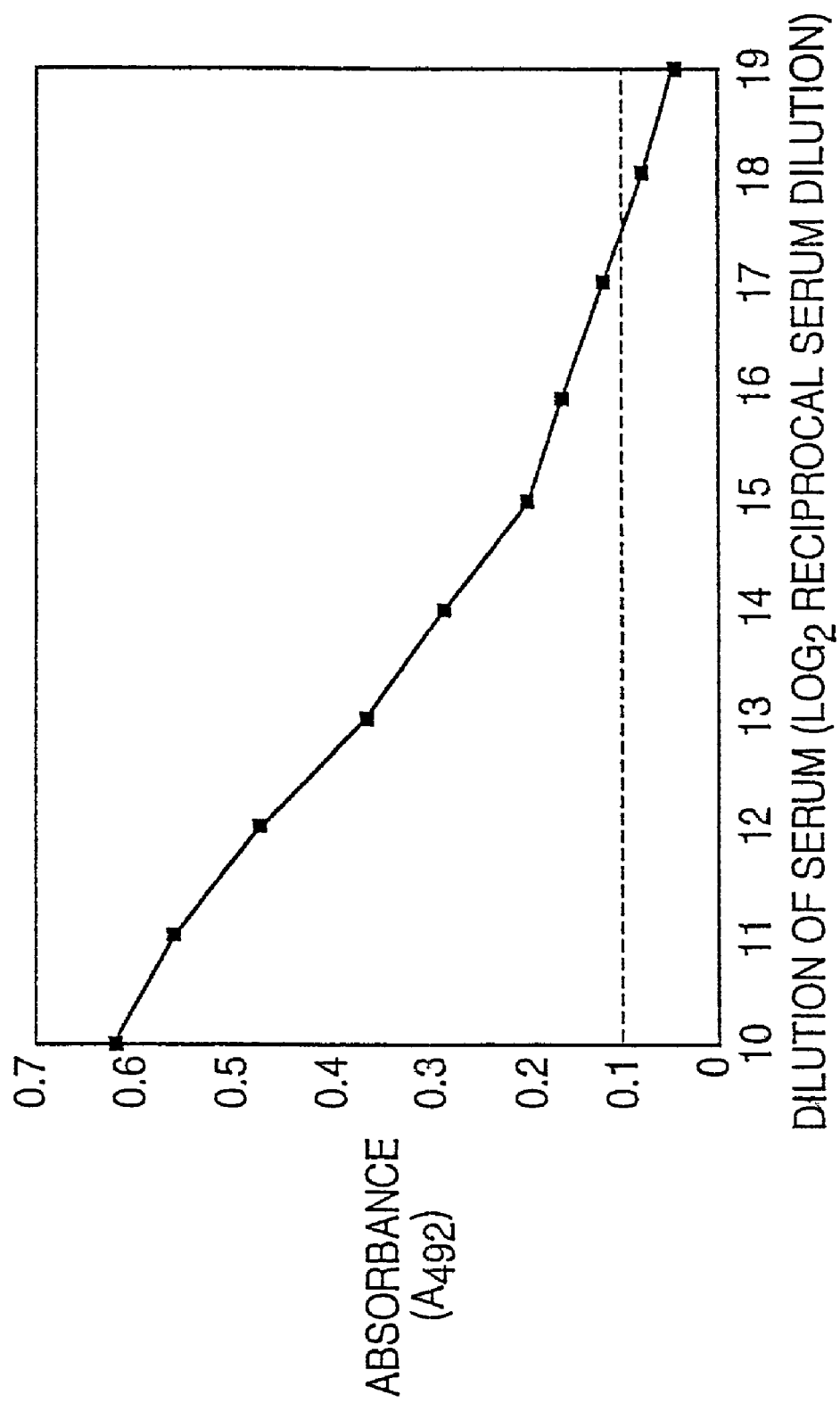

Antibodies against the recombinant protein were raised in rabbits using the same schedule described for producing anti-peptide antibodies. Approximately 10 μg protein was used for each injection. Rabbit serum was screened for anti-cpn10 antibodies by ELISA, using the technique described for screening anti-peptide antibodies with the exception that plates were coated initially with cpn10 (5 μg/ml). The antibody (Ab) titres against cpn10 and against the whole fusion protein (in this case, GST:rcpn10, 5 μg/ml, was bound to the plate) in serum of rabbit #42 are shown in FIG. 7. Titration of a serum sample against cpn10, taken from this rabbit after the 4th booster does, is illustrated in FIG. 8.

B. Pregnancy Termination

In another aspect of the invention, pregnancy may be terminated by administration of antibodies specific for cpn10 to a pregnant subject. The antibodies may be raised against cpn10 or derivatives therefrom. The administration of these antibodies preferably occurs at the pre-implantation stage (1-2 cell stage) or at the peri-implantation stage. Pregnancy termination with anti-cpn10 antibodies is demonstrated below by way of example in a mouse model system. The mouse model system is by way of example only and the method is not limited to mice. The method may be applied to any suitable mammalian species including man.

(i) ANTIBODIES RAISED AGAINST CPN10 PEPTIDES TERMIATES PREGNANCY AT PRE-IMPLANTATION STAGE

Anti-cpn10 Antibodies

The preparation and characterisation of these antibodies have been described. In these experiments, antibodies used were those prepared against the N-terminal peptide (cpnN) and an internal peptide (cpnI); cpnN and cpnI are active in the rosette inhibition test. IgG was precipitated from antiserum by 45% ammonium sulphate and the concentration determined by Lowry and gel electrophoresis. The IgG preparations were tested in an ELISA against the immunising peptide, conjugated to bovine serum albumin. The preparations were also tested for their ability to neutralise activity in mouse pregnancy serum. Various concentrations of antibody were incubated with an equal volume of mouse serum then the mixtures tested for activity in the rosette inhibition test. The lowest concentration of antibody that could completely neutralise EPF activity was determined (see Cavanagh et al., 1994, Eur. J. Biochem. 222 551-560). Ten pg anti-N-peptide Ab neutralised the activity of 1 ml of pregnancy serum while 4 ng anti-I-peptide was needed for complete neutralisation.

Passive Immunisation

Mature outbred male and female Quackenbush mice were caged in pairs at 7.30 a.m and separated at 8.30 a.m. Female mice with vaginal plugs were injected with anti-N-peptide/ovalbumin, anti-I-peptide/ovalbumin or anti-ovalbumin IgG preparations at 9.00 a.m. and 5.00 p.m. on days 1 (day of mating) and 2 of pregnancy. The dose of specific IgG injected in the 2 dose regimen was estimated as approximately 1 mg/mouse/day. On day 7, mice were euthanased with $CO_2$, uteri examined for implanted embryos and the number of corpora lutea (CL) counted. In each group, the number of embryos/CL in the mice treated with the test IgG was compared with the number receiving the same dose of control IgG ($\chi^2$ test).

Results

The results, shown in Table 3, clearly demonstrate that neutralisation of activity in pregnancy serum can adversely affect embryonic viability in the early stages of pregnancy. The ability of antibodies to neutralise cpn10 activity in the rosette inhibition test is an in vitro monitor of their ability in vivo to adversely affect pregnancy.

C. CANCERS AND TUMORS

A further aspect of the invention is the suppression of growth of abnormal cells by the administration of antagonists of cpn10 to a subject. Said abnormal cells or aberrant growth of normal cells include tumour or cancer cells; aberrant growth of normal cells includes diseases such as in psoriasis or Reiter's syndrome. Tumour cells include those from both benign and malignant growths. Cells from malignant diseases such as solid tumours and haematological cancers may also be included. An example of the suppressing effect of tumour cell growth is demonstrated by experiments with murine B16 melanoma and MCA-2 fibrosarcoma cell lines.

(i) EFFECT OF ANTI-CPN10-DERIVED PEPTIDES ANTIBODIES (ABS) ON THE GROWTH OF TUMOR CELLS IN VITRO

Introduction

The following studies investigate the possibility that cpn10, produced by tumour cells in vitro, is also required by these cells for their continued growth.

Methods

Cell Culture

Cell lines were cultured under standard conditions in basal medium. Dulbecco's modification of Eagle's medium (DMEM; ICN Biochemicals Australasia Pty. Ltd. Australia), supplemented with 10% foetal calf serum (FCS, ICN) 20 mM glutamine (ICN) and antibiotics [100 µg/ml streptomycin (ICN), 100 U/ml penicillin (CSL, Melbourne, Australia)], at 37° C. in a humidified atmosphere of 5% $CO_2$ in air.

Cells were maintained in the logarithmic (log) phase of growth. Monolayers were dissociated, after washing in serum-free medium, by a short exposure, at 37° C., to a solution of 0.1% w/v Trypsin and 0.02% w/v versene in calcium and magnesium free balanced salt solution. The action of the trypsin was neutralised with the addition of medium containing 2% v/v FCS and the cells were recovered by centrifuging 200 g for 5 min, washed a further two times in serum free medium, after which they were seeded into culture dishes or 96 well plates (NUNC).

Stocks of cell lines were maintained frozen in liquid $N_2$ at all times.

Preparation of Anti-Peptides Abs for Co-Culture Experiments

Affinity purified anti-N Abs, anti-I Abs and anti-ovalbumin Abs (control antibodies) were exchanged into DMEM and adjusted to a final concentration of 1 mg/ml. The preparations were sterilised by passage through a 0.2 µM cut-off filter (Minisart, Sartorius Gmbh, Goettingen, Germany). As a control medium, DMEM alone was similarly treated.

Co-Culture of Tumor Cells with Anti-Peptides Abs

The murine B16 melanoma and MCA-2 fibrosarcoma cell lines were studied. The cells ($10^3$) were seeded in triplicate, in 0.2 ml culture medium (DMEM+10% FCS (heat inactivated) containing doses of anti-peptide Abs, or control Ab, in the range 62.5-500 µg Ab/ml (final concentration). Cells were similarly seeded into filtered medium containing no antibody. Cultures were examined after a 96 h culture period. Viability was assessed by trypan blue exclusion and uptake of methyl-[$^3$H]thymidine 5'-triphosphate ([$^3$H]thymidine, Amersham International, Amersham, UK) was used to monitor the rate of cell division. Relative [$^3$H]-thymidine uptake for each antibody dose was calculated by expressing the mean cpm incorporated (from triplicate wells) as a percentage of the average cpm incorporated in the wells containing no antibody.

Determination of Cell Viability

Cells dissociated by trypsin, were mixed with an equal volume of 0.1% w/v trypan blue in PBS and spread onto a haemocytometer. Cell viability was calculated as the percentage of cells excluding the dye.

Determination of [$^3$H] Thymidine Uptake

After 80 hours incubation, cells were then cultured for a further 16 hours with 0.5 µCi [$^3$H] thymidine per well. After incubation the supernatant medium of adherent cells was removed and each well was washed twice with warm DMEM. Acid precipitable material was separated by addition of 250 µl ice cold 5% w/v trichloroacetic acid (TCA, BDH Chemicals, Australia Pty Ltd. Kilsyth, Victoria, Australia) to each well (Plate, 1974, J. Exp. Med. 139 851-861). The precipitate was washed twice with TCA and solubilized in 0.3 ml 0.25 N NaOH; 250 µl of this preparation was mixed with 2 ml scintillation cocktail (Emulsifier safe, Packard Instruments Co., Meriden, Conn., USA) and cpm incorporated into acid precipitable material were determined for each well by β-counting.

Immunocytochemistry

Human T-cell leukaemia cells Molt 4 (ATCC CRL 1582) were maintained in log phase in RPMI+10% FCS. Cells were washed three times in RPMI+FCS and incubated ($10^6$ cells) with 10 µg (in 0.1 ml) affinity purified anti-N peptide Ab, anti-I peptide Ab or control antibody (anti-ovalbumin Ab). Control tests contained $10^6$ normal spleen cells. Bound antibody was detected by anti-rabbit biotinylated IgG, F(ab'$_2$) fragment (Amersham), followed by streptavidin-fluorescein according to the manufacturer's instructions. Binding was visualized by UV microscopy.

Results

Tumour cell growth is perturbed by co-culture with anti-cpn10-derived peptides Abs.

Figure 9B:
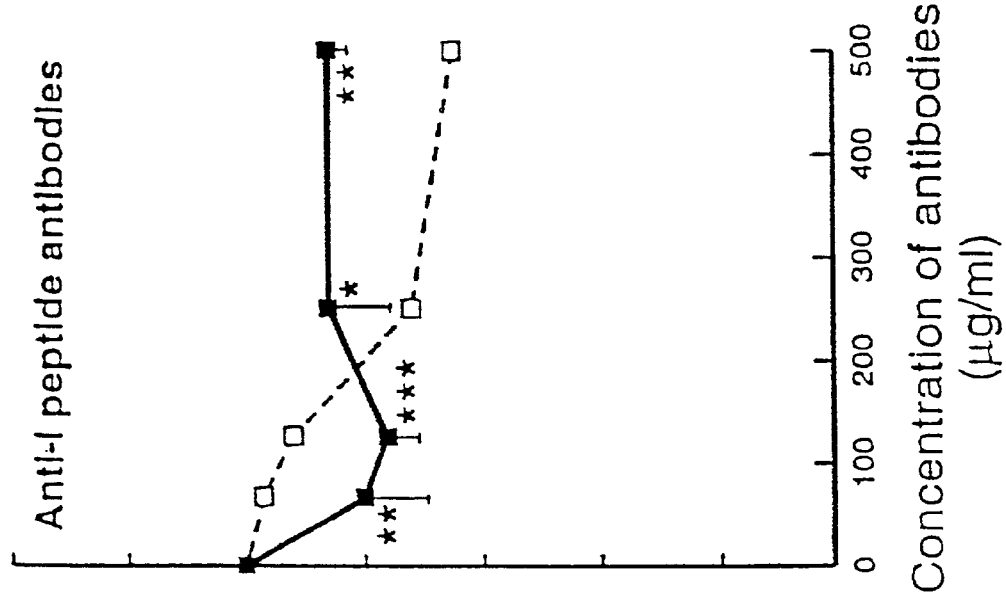
Figure 9A:
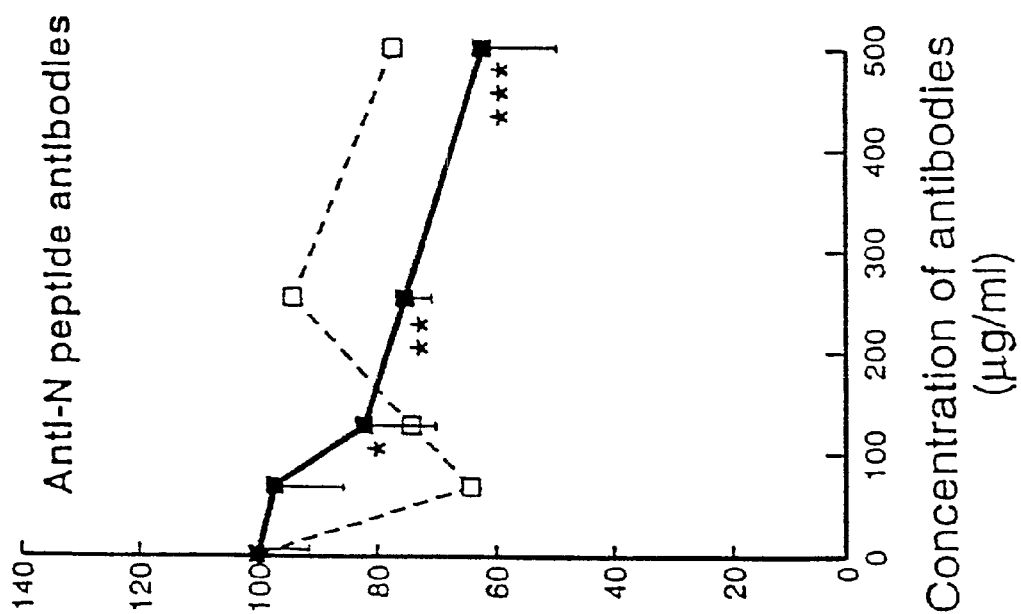
Figure 9C:
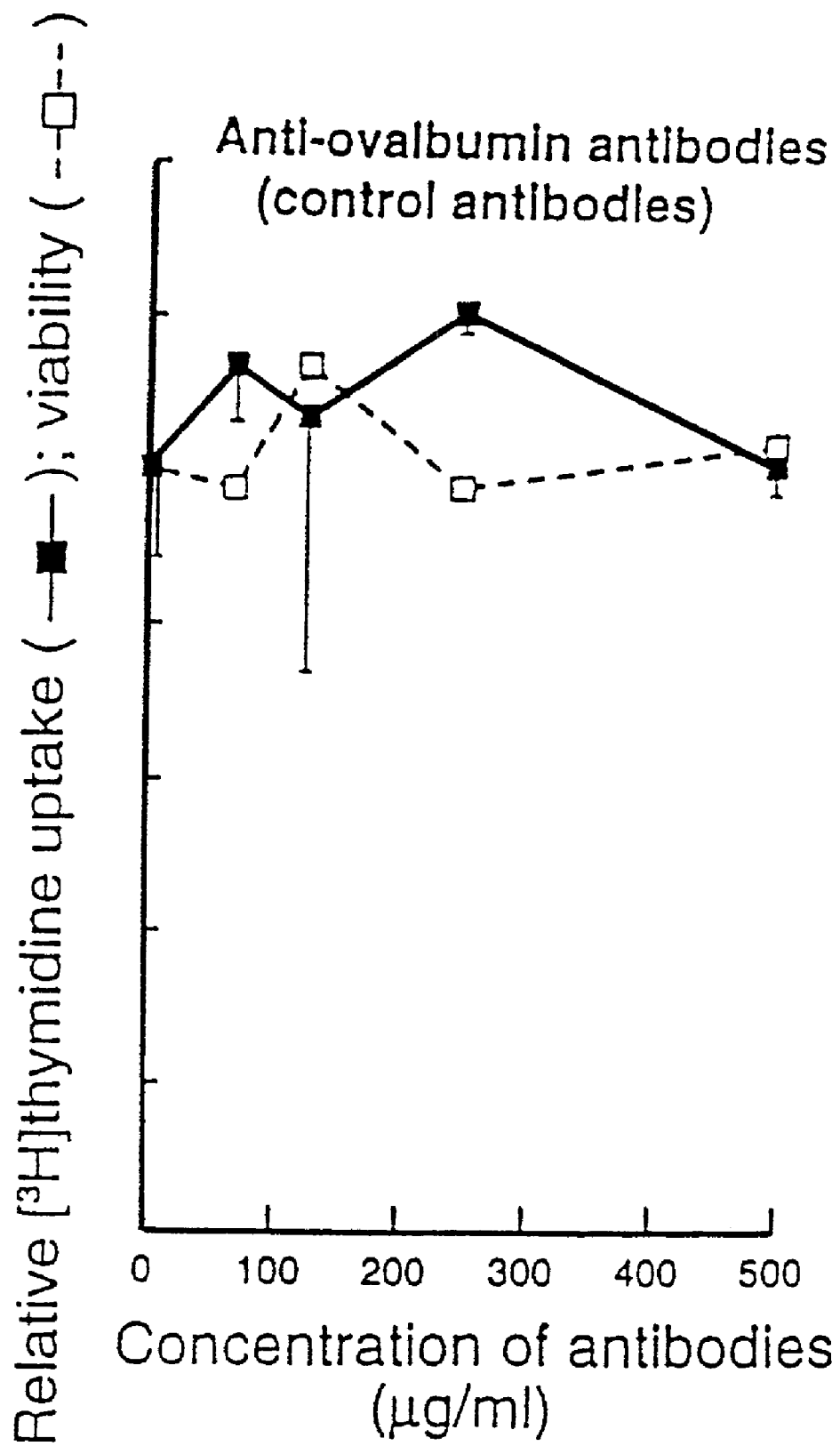

Incubation of B16 melanoma and MCA-2 fibro sarcoma cells in increasing concentrations of anti-peptide Abs resulted in a significant decrease of cell division and increased cell death after 96 h incubation (FIGS. 9a, 9b; 10a, 10b). Incubation of cells in similar concentrations of control Ab had no effect (FIGS. 9c. 10c).

Figure 11:
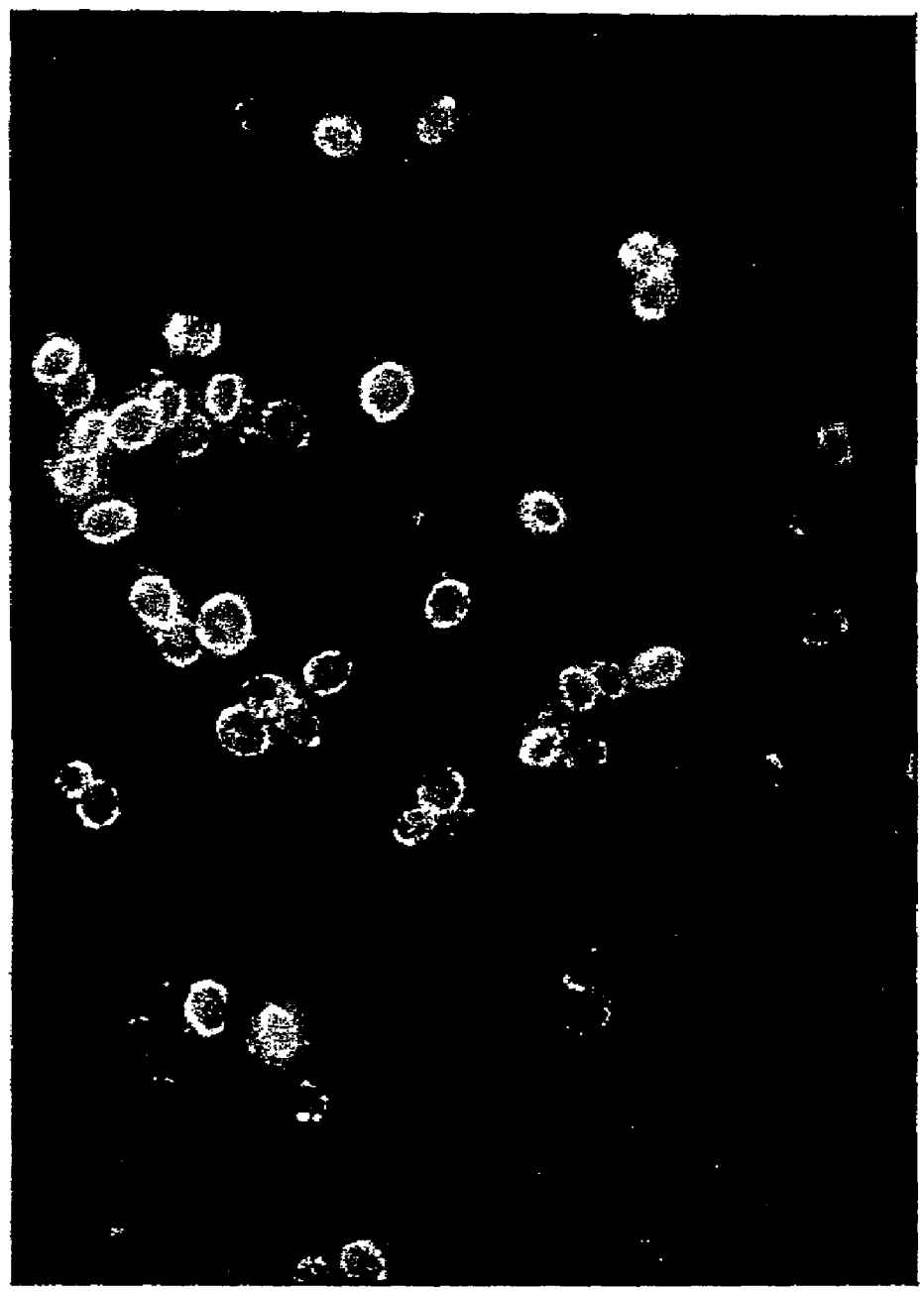

Anti-I peptide antibody bound to cpn10 in the surface of Molt 4 cells. No binding was detected with anti-N peptide or anti-ovalbumin antibody on Molt 4 cells or with any of the abovementioned antibodies on normal spleen cells. This is the first visualization of extracellular cpn10 (FIG. 11).

Conclusion

The studies described here have established that anti-cpn10-derived peptides Abs inhibit the growth of tumour cells. The anti-proliferative effect of culturing B16 and MCA-2 cell lines in increasing doses of anti-peptides Abs is evidence that the growth of these cells is dependent upon continued presence of cpn10. These studies have established that the tumour cells require cpn10 for proliferation in vitro.

OTHER ASPECTS OF THE INVENTION

The abovementioned N-terminal fragment and internal fragment are regions of the molecule which are active in the rosette inhibition test and therefore function as active centres.

Pharmacological antagonists can be constructed, using conventional means, by modification of the structure of these active centres, so that binding to target sites. e.g. tumour cells, may occur without target activation. By interfering with the action of the whole cpn10 molecule on tumour cells, these antagonists will mimic the anti-proliferative effect described above for anti-cpn10 antibodies.

The invention also includes within its scope an assay for measuring anti-cpn10 antibody in a sample including the steps of:

(1) reacting substantially purified cpn10 with the sample; and
(2) determination of the amount of anti-cpn10 antibody in the sample by determing the binding between the antibody and cpn10.

It will also he appreciated from the foregoing that data is available (e.g. Quinn et. al., 1992, Cancer Immunol. Immunother. 34 265-271) that anti-EPF antibodies are useful in suppression of tumour growth in a mouse model. Such data supports the assertion that anti-EPF antibodies will suppress tumour growth in Vivo or in vitro.

The dosages utlised in the administration of antagonists or antibodies are in the range of 1-1000 (more preferably 50-200) µg/kg of body weight for antagonists and 1-1000 (more preferably 50-200) mg/kg of body weight for antibodies. These dosages are based on a molecule which has the same molecular weight as cpn10 and dosages should be adjusted accordingly.

TABLE 1

| Ag | Dose (µg/injection) |
| --- | --- |
| I-peptide | 200 |
| N-peptide | 400 |
| Ovalbumin | 500 |

TABLE 2

| | | TITRE 1 log₂ reciprocal serm dilution | | |
| --- | --- | --- | --- | --- |
| Anti-serum | Test antigen | Pre Column (serum before column) | Bound (fractions) | Unbound (serum after column) |
| Anti-N ovalbumin | N-peptide | 15 | 18 | 11 |
| Anti-ovalbumin | I-peptide | 13 | 19 | 10 |
| Anti-ovalbumin | Ovalbumin | 19 | 25 | >17 |

TABLE 3

| Antibody (total dose 2 mg/ mouse) | No. of animals in group | Corporalutea/ mouse (mean ± sem) | Embryo/ mouse (mean ± sem) | p* |
| --- | --- | --- | --- | --- |
| Anti-N-peptide-ovalbumin | 6 | 19.1 ± 1.2 | 10.6 ± 3.8 | <0.05 |
| Anti-I-peptide-ovalbumin | 6 | 20.8 ± 0.8 | 17.1 ± 1.1 | <0.02 |
| Anti-ovalbumin | 5 | 17.8 ± 1.0 | 16.8 ± 0.5 | NS |

Table Legends

Table 1

Dose of antigen per injection administered to rabbits in the preparation of antibodies.

Table 2

Titre of affinity purified anti-cpn10 peptide antibodies and control anti-ovalbumin antibodies.

Table 3

Effect of passive immunization of confirmed-mated mice at days 1 and 2 p.c., with antibodies to cpn10-derived peptides, on the number of implanted embryos and corpora lutea present at day 7 p.c.

*(Heteroscedastic t-test).

FIGURE LEGENDS

FIG. 1a Purification of EPF. Heat extracted human platelets (100 units) were fractionated on SP-Sephadex and Heparin Sepharose, then applied to a TSK-Phenyl 5PW column and eluted with a reverse salt gradient. Fractions were tested in the rosette inhibition test (based on EPF's capacity to augment the rosette inhibiting activity of an immunosuppressive antilymphocyte serum).

FIG. 1b Active fractions (⊓) from (a) were fractionated by RP-HPLC-1.

FIG. 1c Active fractions (⊓) from (b) were fractionated by RP-HPLC-2.

FIG. 1d Active fractions (⊓) from (c) were fractionated by RP-HPLC-3.

Figure 1E:
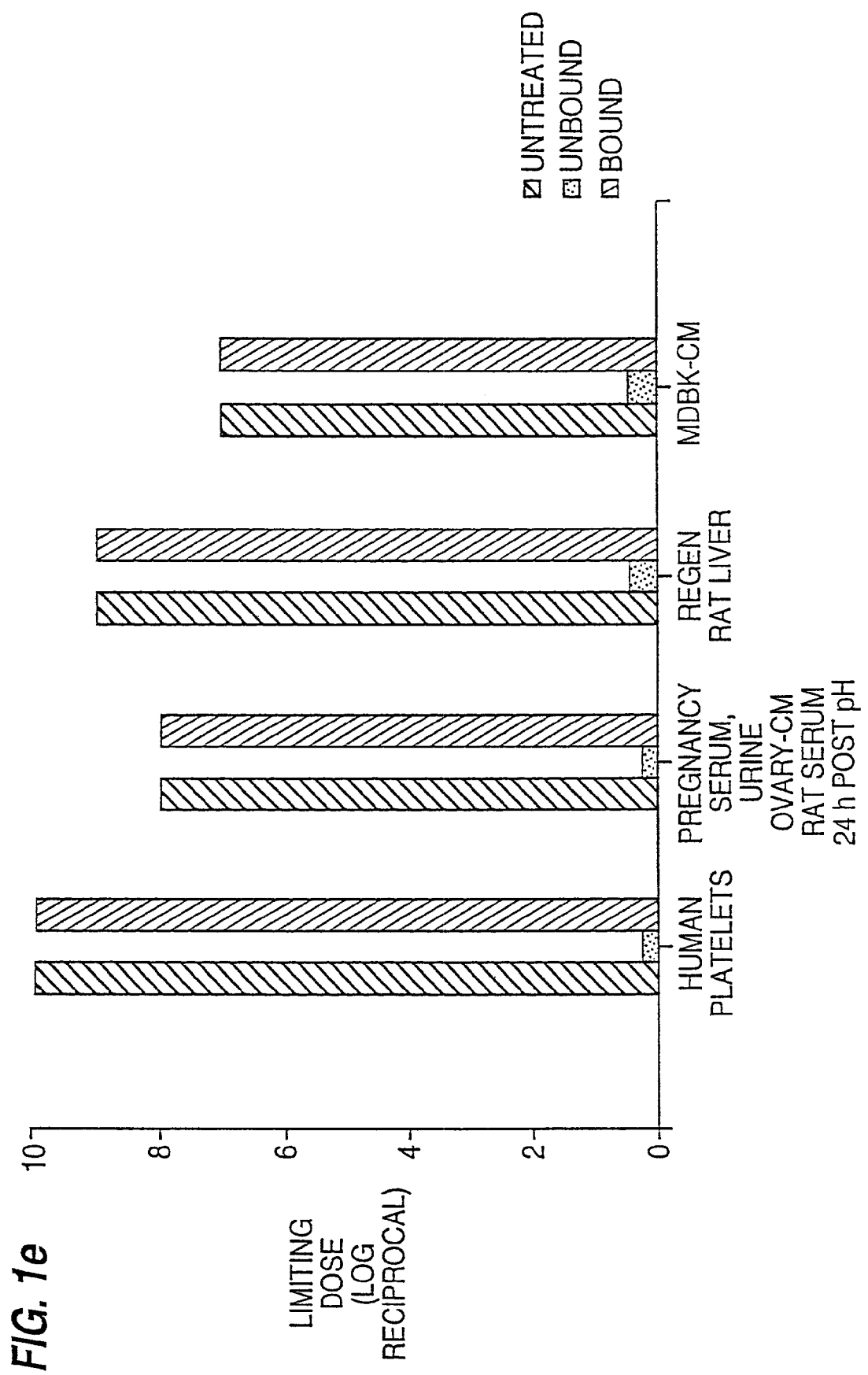

FIG. 1e Interaction of immobilised monoclonal anti-EPF antibody 5/341 with active fractions from (d) and equivalent fractions from human pregnancy serum, 6 d gestation (10 ml): human pregnancy urine, up to 1 month gestation (10 liter); medium conditioned by oestrous mouse ovaries (100) stimulated with prolactin and mouse embryo-conditioned medium (ovary CM); serum free medium conditioned by the bovine kidney cell line MDBK (MDBK-CM: ATCC CCL 22, 10 liter); rat serum obtained 24 h post-partial hepatectomy (post-pH, 10 ml), rat liver obtained 24 h post-pH (40 g): all fractionated as in (a) to (d). Anti-EPF bound and unbound fractions were tested in the rosette inhibition test, specificity was demonstrated by comparison with a parallel experiment using irrelevant antibody in which activity was not bound.

Figure 2A:
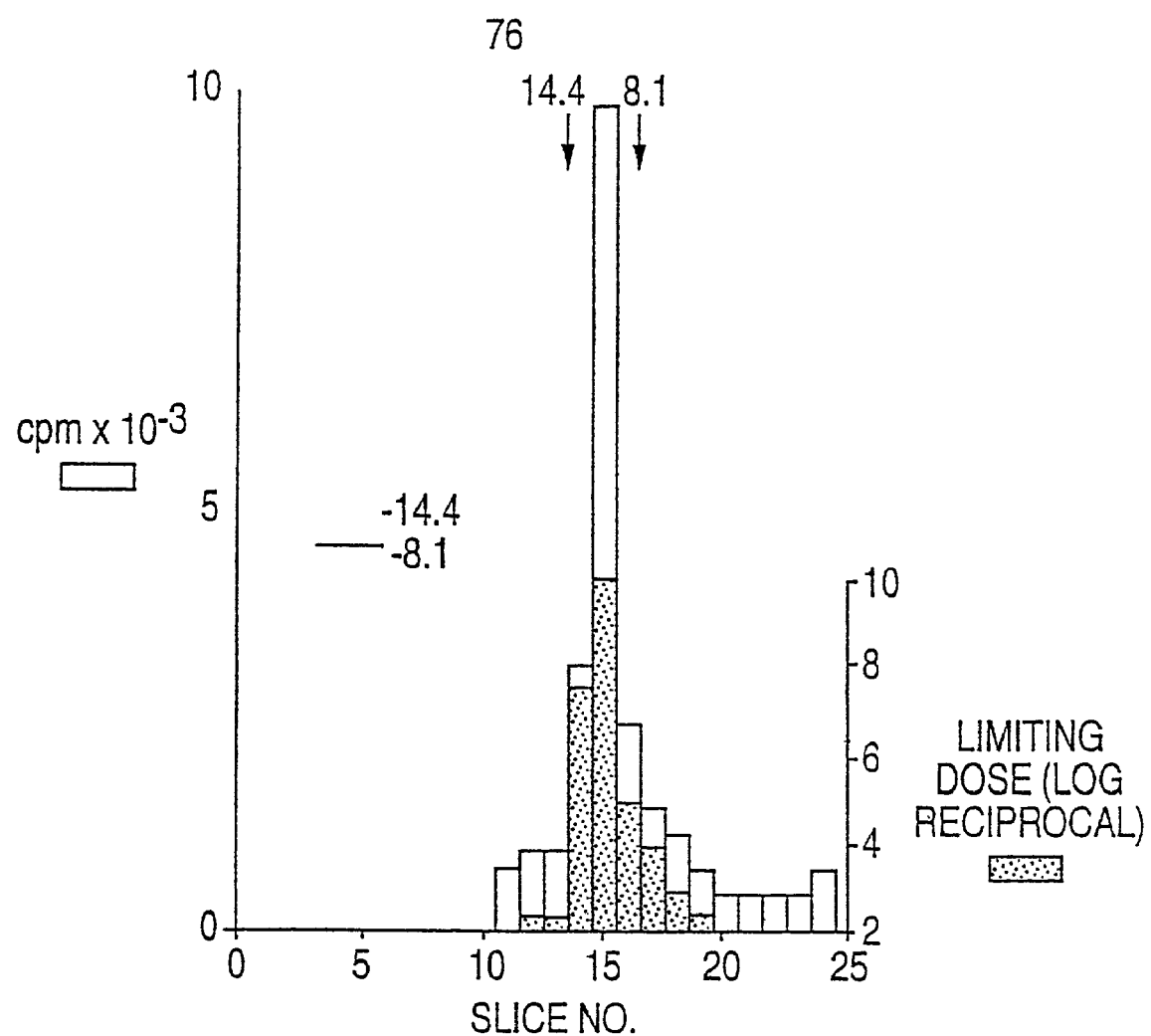

FIG. 2a Analysis of EPF purified from 300 units human platelets as in FIG. 1A. Determination of monomeric size. Iodinated EPF was fractionated by SDS-PAGE,[29] the gel sliced (2 mm wide slices) and the distribution of radioactivity and biological activity compared. (Inset) Direct Coomassie Blue staining of the same preparation.

Figure 2B:
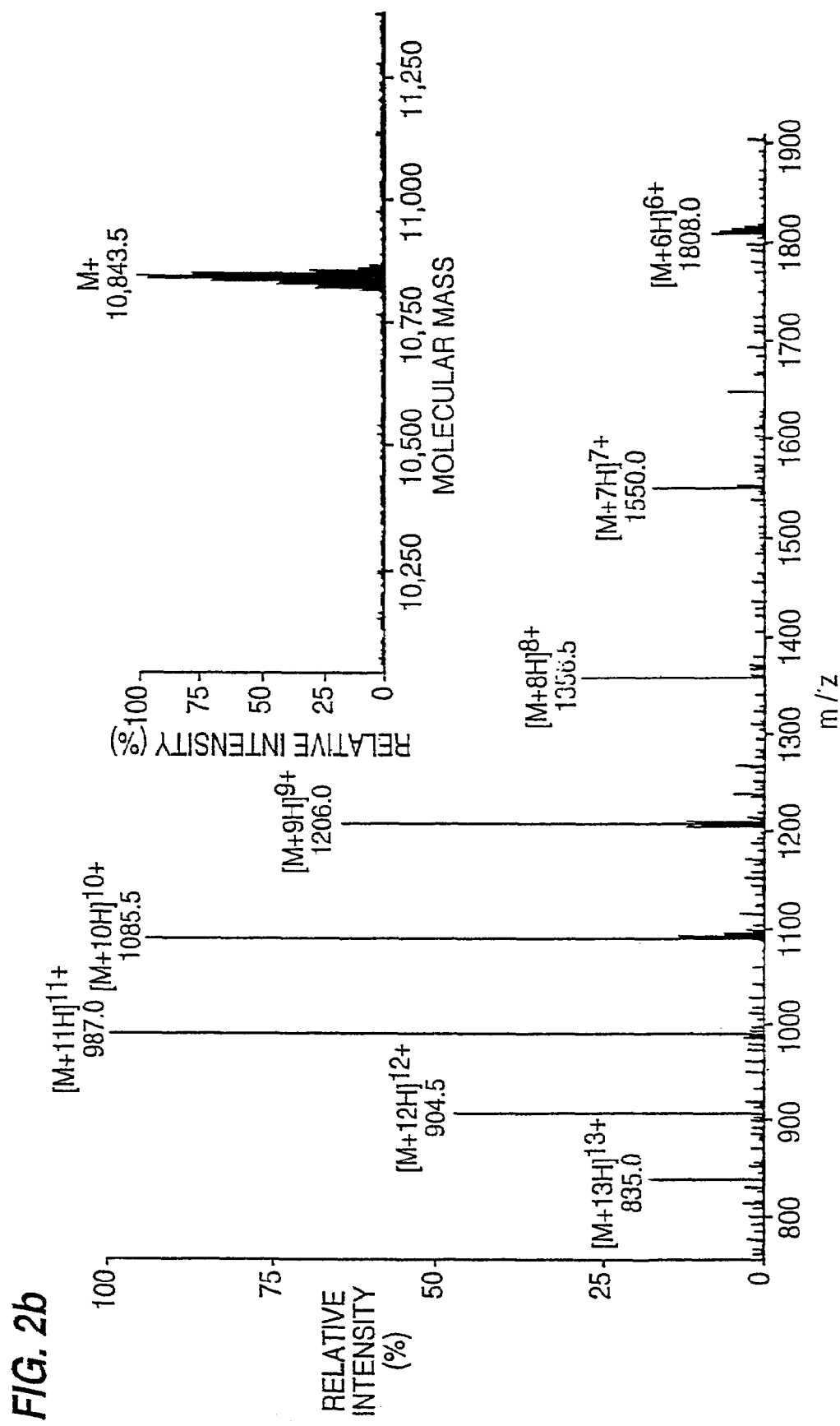

FIG. 2b Ion-spray mass spectrum of EPF, displayed as multiply protonated molecular ions. (Inset) Computer reconstruction as molecular mass.

FIG. 2c Amino acid sequence (single letter code) of peptides derived from human EPF, compared with rat cpn10 (underlined). EPF was digested with endoproteinase lycC and endoproteinase glu C, the resultant peptides separated by RP-HPLC and sequenced. The sequence of individual fragments is shown: all except 74-101 were derived from the lys digest (SEQ ID NOS: 22-25 are shown in this figure).

FIG. 3 Interaction of EPF and cpn60 (groEL).

FIG. 3a Peak fractions in the excluded volume of a TSK G3000SW gel permeation column, following application of a cpn60-EPF mixture +$Mg^{2+}$ ATP, were analysed by SDS-PAGE (Schagger et al., 1987) and stained with silver (Morrissey, 1981). Left lane, +ATP; right lane −ATP. (Cpn60 is a decatetramer, M, 840 000; column exclusion limit >300 000. Higher $M_r$ bands on SDS gel are oligomeric forms of groEL).

FIG. 3b Immobilised cpn60 was mixed with human pregnancy serum (6 d gestation) in thke presence or absence of $Mg^{2+}$ ATP. Unbound and bound fractions (the latter recovered from the gel by removal of ATP with EDTA) were then tested in the rosette inhibition test. Results are expressed as limiting dose, the highest dilution of sample giving a positive result in the rosette inhibition test.

Figure 4B:
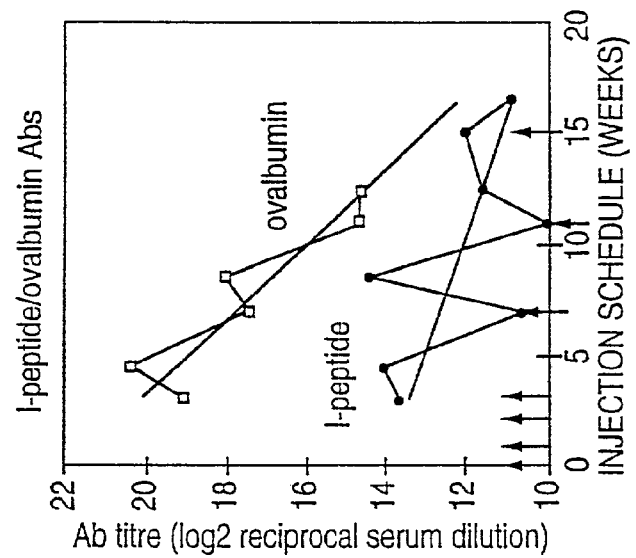
Figure 4A:
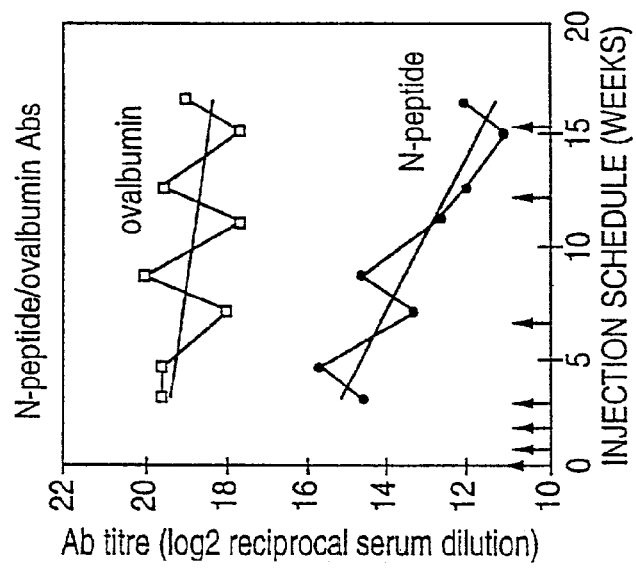

FIGS. 4a, FIG. 4b, FIG. 4c Rabbit antibodies to cpn10-peptide/ovalbumin conjugates. Antibodies tested in an ELISA against immunising antigens.

FIG. 5 Anti-N-peptide. anti-EPF #816, anti-EPF #810 and control anti-ovalbumin antibodies (100 ng/ml) were tested in an ELISA against ▬ N-peptide (5 μg/ml) and ☐ EPF/cpn10 (1 μg/ml). Bound IgG was detected by the biotin-streptavidin system (Amersham) with o-phenylene diamine as substrate. Absorbance was read at 492 nm.

FIG. 6a pRM1

FIG. 6b pRM2

FIG. 6c pRM3

FIG. 7 Preparation of antibodies to cpn10. Fusion protein (GST:rcpn10).

FIG. 8 Detection of anti-cpn10 antibodies in rabbit serum by ELISA. Serum harvested after the 4th booster dose of antigen.

FIG. 9 Relative [$^3$H]thymidine uptake (-■-) and viability (-☐-) of B16 melanoma cells after incubation for 96 h with anti-cpn10-derived peptide antibodies. Proliferation was assessed by uptake of [$^3$H]thymidine into cells incubated with antibody, expressed as a percentage of [$^3$H]thymidine incubated without antibody.

* $p<0.05$,  $p<0.01$, * $p<0.001$, (Student's t test) n=3.

FIG. 10 Relative [$^3$H]thymidine uptake (-■-) and viability (-☐-) of MCA-2 fibrosarcoma cells after incubation for 96 h with anti-cpn10-derived peptide antibodies. Proliferation was assessed by uptake of [$^3$H]thymidine into cells incubated with antibody, expressed as a percentage of [$^3$H] thymidine incubated without antibody.

*p $<0.05$,  $p<0.01$, * $p<0.001$, (Student's t test) n=3.

FIG. 11 Anti-cpn10 I-peptide Abs detect cpn10 on the surface of human Molt 4 leukaemia cells.

What is claimed is:

1. A recombinant chaperonin 10 (cpn 10) consisting of the sequence GSMAGQAFRKFLPLFDRVLVERSAAETVTKGGIMLPEKSQGKVLQATV VAVGSGSKGKGGEIQPVSVKVGDKVLLPEYGGT-KVVLDDKDYFLFRD GDILGKYVD (SEQ ID NO:21).

2. An isolated chaperonin 10 (cpn 10) consisting of the sequence GSMAGQAFRKFLPLFDRVLVERSAAETVTKGGIMLPEKSQGKVLQATV VAVGSGSKGKGGEIQPVSVKVGDKVLLPEYGGT-KVVLDDKDYFLFRD GDILGKYVD (SEQ ID NO:21).

3. A purified peptide consisting of the amino acid sequence selected from the group consisting of AGQAFRKFLPL (SEQ ID NO:1),
acetyl-AGQAFIRKFLPL (SEQ ID NO:2), and
EKSQGKVLQAT (SEQ ID NO:3).

4. The peptide according to claim 3, consisting of amino acid sequence AGQAFRKFLPL (SEQ ID NO:1).

5. The peptide according to claim 3, consisting of amino acid sequence acetyl-AGQAFIRKFLPL (SEQ ID NO:2).

6. The peptide according to claim 3, consisting of an amino acid sequence EKSQGKVLQAT (SEQ ID NO:3).

* * * * *

SEQUENCE LISTING (1) GENERAL INFORMATION:

(iii) NUMBER OF SEQUENCES: 26

(2) INFORMATION FOR SEQ ID NO: 1:

(i) SEQUENCE CHARACTERISTICS:
      (A) LENGTH: 11 amino acids
      (B) TYPE: amino acid
      (C) STRANDEDNESS: single
      (D) TOPOLOGY: linear (xi) SEQUENCE DESCRIPTION: SEQ ID NO: 1:

Ala Gly Gln Ala Phe Arg Lys Phe Leu Pro Leu
1          5               10

(2) INFORMATION FOR SEQ ID NO: 2:

(i) SEQUENCE CHARACTERISTICS:
      (A) LENGTH: 12 amino acids
      (B) TYPE: amino acid
      (C) STRANDEDNESS: single
      (D) TOPOLOGY: linear

```
        (ix) FEATURE:
              (A) NAME/KEY: Modified-site
              (B) LOCATION: 1
              (D) OTHER INFORMATION: /product= "Other"
                    /note= "The Xaa at position 1 is acetyl."

(xi) SEQUENCE DESCRIPTION: SEQ ID NO: 2:

Xaa Ala Gly Gln Ala Phe Arg Lys Phe Leu Pro Leu
1               5                   10

(2) INFORMATION FOR SEQ ID NO: 3:

(i) SEQUENCE CHARACTERISTICS:
              (A) LENGTH: 11 amino acids
              (B) TYPE: amino acid
              (C) STRANDEDNESS: single
              (D) TOPOLOGY: linear (xi) SEQUENCE DESCRIPTION: SEQ ID NO: 3:

Glu Lys Ser Gln Gly Lys Val Leu Gln Ala Thr
1               5                   10

(2) INFORMATION FOR SEQ ID NO: 4:

(i) SEQUENCE CHARACTERISTICS:
              (A) LENGTH: 13 amino acids
              (B) TYPE: amino acid
              (C) STRANDEDNESS: single
              (D) TOPOLOGY: linear (xi) SEQUENCE DESCRIPTION: SEQ ID NO: 4:

Xaa Ala Gly Gln Ala Phe Arg Lys Phe Leu Pro Leu Ala
1               5                   10

(2) INFORMATION FOR SEQ ID NO: 5:

(i) SEQUENCE CHARACTERISTICS:
              (A) LENGTH: 12 amino acids
              (B) TYPE: amino acid
              (C) STRANDEDNESS: single
              (D) TOPOLOGY: linear (xi) SEQUENCE DESCRIPTION: SEQ ID NO: 5:

Ala Gly Gln Ala Phe Arg Lys Phe Leu Pro Leu Ala
1               5                   10

(2) INFORMATION FOR SEQ ID NO: 6:

(i) SEQUENCE CHARACTERISTICS:
              (A) LENGTH: 12 amino acids
              (B) TYPE: amino acid
              (C) STRANDEDNESS: single
              (D) TOPOLOGY: linear (xi) SEQUENCE DESCRIPTION: SEQ ID NO: 6:

Xaa Ala Gly Gln Ala Phe Arg Lys Phe Leu Pro Leu
1               5                   10

(2) INFORMATION FOR SEQ ID NO: 7:

(i) SEQUENCE CHARACTERISTICS:
              (A) LENGTH: 14 amino acids
              (B) TYPE: amino acid
              (C) STRANDEDNESS: single
              (D) TOPOLOGY: linear (ix) FEATURE:
              (A) NAME/KEY: Modified-site
```

```
            (B) LOCATION: 1
            (D) OTHER INFORMATION: /product= "Other"
                /note= "The Xaa at position 1 is acetyl."

(xi) SEQUENCE DESCRIPTION: SEQ ID NO: 7:

Xaa Xaa Ala Gly Gln Ala Phe Arg Lys Phe Leu Pro Leu Xaa
1               5                   10

(2) INFORMATION FOR SEQ ID NO: 8:

(i) SEQUENCE CHARACTERISTICS:
        (A) LENGTH: 13 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /product= "Other"
            /note= "The Xaa at position 1 is acetyl."

(xi) SEQUENCE DESCRIPTION: SEQ ID NO: 8:

Xaa Ala Gly Gln Ala Phe Arg Lys Phe Leu Pro Leu Xaa
1               5                   10

(2) INFORMATION FOR SEQ ID NO: 9:

(i) SEQUENCE CHARACTERISTICS:
        (A) LENGTH: 13 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /product= "Other"
            /note= "The Xaa at position 1 is acetyl."

(xi) SEQUENCE DESCRIPTION: SEQ ID NO: 9:

Xaa Xaa Ala Gly Gln Ala Phe Arg Lys Phe Leu Pro Leu
1               5                   10

(2) INFORMATION FOR SEQ ID NO: 10:

(i) SEQUENCE CHARACTERISTICS:
        (A) LENGTH: 13 amino acids
        (B) TYPE: amino acid
        (C) STRANDEDNESS: single
        (D) TOPOLOGY: linear (xi) SEQUENCE DESCRIPTION: SEQ ID NO: 10:

Xaa Glu Lys Ser Gln Gly Lys Val Leu Gln Ala Thr Xaa
1               5                   10

(2) INFORMATION FOR SEQ ID NO: 11:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO: 11:

Glu Lys Ser Gln Gly Lys Val Leu Gln Ala Thr Xaa
1               5                   10

(2) INFORMATION FOR SEQ ID NO: 12:
```

```
    (i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO: 12:

Xaa Glu Lys Ser Gln Gly Lys Val Leu Gln Ala Thr
1               5                   10

(2) INFORMATION FOR SEQ ID NO: 13:

(i) SEQUENCE CHARACTERISTICS:
        (A) LENGTH: 13 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /product= "Other"
            /note= "The Xaa at position 1 is acetyl."

(xi) SEQUENCE DESCRIPTION: SEQ ID NO: 13:

Xaa Ala Gly Gln Ala Phe Arg Lys Phe Leu Pro Leu Cys
1               5                   10

(2) INFORMATION FOR SEQ ID NO: 14:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO: 14:

Glu Lys Ser Gln Gly Lys Val Leu Gln Ala Thr Cys
1               5                   10

(2) INFORMATION FOR SEQ ID NO: 15:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 15:

Val Leu Asp Asp Lys Asp Tyr Phe Leu
1               5

(2) INFORMATION FOR SEQ ID NO: 16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 16:

ARRAARTART CYTTRTCRTC                                         20

(2) INFORMATION FOR SEQ ID NO: 17:

(i) SEQUENCE CHARACTERISTICS:
        (A) LENGTH: 17 base pairs
        (B) TYPE: nucleic acid
```

```
        (C) STRANDEDNESS: single
        (D) TOPOLOGY: linear (xi) SEQUENCE DESCRIPTION: SEQ ID NO: 17:

CAGGAAACAG CTATGAC                                                          17

(2) INFORMATION FOR SEQ ID NO: 18:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 18:

GTAAAACGAC GGCCAGT                                                          17

(2) INFORMATION FOR SEQ ID NO: 19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 19:

GCGCGGATCC ATGGCAGGAC AAGCGTTTAG                                             30

(2) INFORMATION FOR SEQ ID NO: 20:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 20:

ATATGAATTC AGTCTACGTA CTTTCC                                                26

(2) INFORMATION FOR SEQ ID NO: 21:

(i) SEQUENCE CHARACTERISTICS:
        (A) LENGTH: 104 amino acids
        (B) TYPE: amino acid
        (C) STRANDEDNESS: single
        (D) TOPOLOGY: linear (xi) SEQUENCE DESCRIPTION: SEQ ID NO: 21:

Gly Ser Met Ala Gly Gln Ala Phe Arg Lys Phe Leu Pro Leu Phe Asp
1               5                   10                  15

Arg Val Leu Val Glu Arg Ser Ala Ala Glu Thr Val Thr Lys Gly Gly
            20                  25                  30

Ile Met Leu Pro Glu Lys Ser Gln Gly Lys Val Leu Gln Ala Thr Val
        35                  40                  45

Val Ala Val Gly Ser Gly Ser Lys Gly Lys Gly Gly Glu Ile Gln Pro
    50                  55                  60

Val Ser Val Lys Val Gly Asp Lys Val Leu Leu Pro Glu Tyr Gly Gly
65                  70                  75                  80

Thr Lys Val Val Leu Asp Asp Lys Asp Tyr Phe Leu Phe Arg Asp Gly
                85                  90                  95

Asp Ile Leu Gly Lys Tyr Val Asp
            100
```

(2) INFORMATION FOR SEQ ID NO: 22:

(i) SEQUENCE CHARACTERISTICS:
        (A) LENGTH: 43 amino acids
        (B) TYPE: amino acid
        (C) STRANDEDNESS: single
        (D) TOPOLOGY: linear (xi) SEQUENCE DESCRIPTION: SEQ ID NO: 22:

```
Lys Val Leu Xaa Ala Thr Val Val Ala Val Gly Ser Gly Ser Lys Glu
1               5                   10                  15

Tyr Gly Gly Thr Lys Val Val Xaa Xaa Xaa Xaa Asp Xaa Phe Leu Phe
            20                  25                  30

Arg Asp Gly Asp Ile Leu Gly Lys Tyr Val Asp
        35                  40
```

(2) INFORMATION FOR SEQ ID NO: 23:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 23:

```
Lys Ser Gln Gly Lys Val Leu Gln Ala Thr Val Val Ala Val Gly Xaa
1               5                   10                  15

Gly Xaa Lys Val Leu Leu Pro Glu Tyr Gly Gly Thr
            20                  25
```

(2) INFORMATION FOR SEQ ID NO: 24:

(i) SEQUENCE CHARACTERISTICS:
        (A) LENGTH: 47 amino acids
        (B) TYPE: amino acid
        (C) STRANDEDNESS: single
        (D) TOPOLOGY: linear (xi) SEQUENCE DESCRIPTION: SEQ ID NO: 24:

```
Lys Phe Leu Pro Leu Phe Asp Arg Val Leu Val Glu Lys Gly Gly Ile
1               5                   10                  15

Met Leu Pro Glu Lys Xaa Gln Gly Lys Val Val Leu Asp Asp Lys Asp
            20                  25                  30

Tyr Phe Leu Phe Arg Asp Gly Asp Ile Leu Gly Lys Tyr Val Asp
        35                  40                  45
```

(2) INFORMATION FOR SEQ ID NO: 25:

(i) SEQUENCE CHARACTERISTICS:
        (A) LENGTH: 102 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /product= "Other"
           /note= "The Xaa at position 1 is acetyl."

(xi) SEQUENCE DESCRIPTION: SEQ ID NO: 25:

```
Xaa Ala Gln Ala Gly Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30
```

```
Pro Leu Glu Lys Ser Gln Gly Lys Val Leu Gln Ala Thr Val Val Ala
        35              40              45

Val Gly Ser Gly Gly Lys Gly Lys Gly Gly Glu Ile Gln Pro Val Xaa
        50              55              60

Xaa Lys Xaa Gly Xaa Xaa Val Leu Leu Pro Glu Tyr Gly Gly Thr Lys
65              70              75              80

Val Val Leu Asp Asp Lys Asp Tyr Phe Leu Phe Arg Asp Gly Asp Ile
            85              90              95

Leu Gly Lys Tyr Val Asp
            100

(2) INFORMATION FOR SEQ ID NO: 26:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO: 26:

Ala Gly Gln Ala Phe Arg Lys Phe Leu Pro Leu Cys
1               5               10
```